United States Patent

Hubbell et al.

[11] Patent Number: 6,153,211
[45] Date of Patent: Nov. 28, 2000

[54] BIODEGRADABLE MACROMERS FOR THE CONTROLLED RELEASE OF BIOLOGICALLY ACTIVE SUBSTANCES

[75] Inventors: Jeffrey A. Hubbell, Zumikon, Switzerland; Mark T. Kieras, Newburyport, Mass.; Eyal S. Ron, Lexington, Mass.; Stephen C. Rowe, Wellesley, Mass.

[73] Assignee: InfiMed, Inc., Cambridge, Mass.

[21] Appl. No.: 09/118,242

[22] Filed: Jul. 17, 1998

Related U.S. Application Data

[60] Provisional application No. 60/053,029, Jul. 18, 1997.

[51] Int. Cl.[7] .............................. A61F 2/00; A61F 13/00; A61K 9/22
[52] U.S. Cl. ..................... 424/426; 424/422; 424/433; 604/890.1; 604/891.1
[58] Field of Search ................................ 424/426, 422, 424/433; 604/890.1, 891.1

[56] References Cited

U.S. PATENT DOCUMENTS

| | | | |
|---|---|---|---|
| 4,741,872 | 5/1988 | De Luca et al. | 264/4.7 |
| 4,804,691 | 2/1989 | English et al. | 523/118 |
| 4,898,734 | 2/1990 | Mathiowitz et al. | 424/426 |
| 5,149,543 | 9/1992 | Cohen et al. | 424/499 |
| 5,232,984 | 8/1993 | Hubbell et al. | 525/54.1 |
| 5,252,701 | 10/1993 | Jarrett et al. | 528/354 |
| 5,320,624 | 6/1994 | Kaplan et al. | 606/77 |
| 5,380,536 | 1/1995 | Hubbell et al. | 424/497 |
| 5,410,016 | 4/1995 | Hubbell et al. | 528/354 |
| 5,462,990 | 10/1995 | Hubbell et al. | 525/54.1 |
| 5,529,914 | 6/1996 | Hubbell et al. | 435/182 |
| 5,567,435 | 10/1996 | Hubbell et al. | 424/426 |
| 5,567,440 | 10/1996 | Hubbell et al. | 424/484 |
| 5,573,934 | 11/1996 | Hubbell et al. | 435/177 |
| 5,595,971 | 1/1997 | Mitchell | 514/12 |
| 5,626,863 | 5/1997 | Hubbell et al. | 424/426 |
| 5,627,233 | 5/1997 | Hubbell et al. | 525/54.1 |
| 5,631,015 | 5/1997 | Bezwada et al. | 424/422 |
| 5,654,007 | 8/1997 | Johnson et al. | 424/489 |
| 5,736,371 | 4/1998 | Samain et al. | 435/179 |
| 5,753,219 | 5/1998 | Cleland et al. | 424/85.7 |

FOREIGN PATENT DOCUMENTS

| | | |
|---|---|---|
| 92/06678 | 4/1992 | WIPO . |
| 95/31479 | 11/1995 | WIPO . |
| 96/11671 | 4/1996 | WIPO . |
| 96/29370 | 9/1996 | WIPO . |
| 96/32149 | 10/1996 | WIPO . |
| 97/05185 | 2/1997 | WIPO . |
| 97/41833 | 11/1997 | WIPO . |
| 97/44013 | 11/1997 | WIPO . |

OTHER PUBLICATIONS

Clark et al., "Long–acting Growth Hormones Produced by Conjugation with Polyethylene Glycol," The Journal of Biological Chemistry 271(36):21969–21977 (1996).

(List continued on next page.)

*Primary Examiner*—Thurman K. Page
*Assistant Examiner*—Todd D. Ware
*Attorney, Agent, or Firm*—Clark & Elbing LLP; Kristina Bieker-Brady

[57] ABSTRACT

A method for delivering a biologically active substance including the steps of: (a) combining said biologically active substance with a macromer; (b) forming a mixture of the combination formed in step (a); (c) polymerizing said mixture to form articles; and (d) administering said articles, or a portion thereof, to a mammal, where step (c) takes place in the absence of a polymerizable monovinyl monomer, is disclosed.

14 Claims, 14 Drawing Sheets

LARGE PARTICLE

SMALL PARTICLE

LOW LOADING (<15%)
BURST IS AN ISSUE

SUSPENSION OF PROTEIN PARTICLES

HOMOGENOUS PROTEIN SOLUTION

OTHER PUBLICATIONS

Cleland, "Protein Delivery from Biodegradable Microspheres," Pharmaceutical Biotechnology, Chapter 1, Protein Delivery Physical Systems (Sanders and Hendren, eds.) Plenum Press, New York pp. 1–43 (1997).

Gonda, "Aerosols for Delivery of Therapeutic and Diagnostic Agents to the Respiratory Tract," Critical Reviews in Therapeutic Drug Carrier Systems 6(4):273–313 (1990).

Hill–West et al., "Inhibition of thrombosis and intimal thickening by in situ photopolymerication of thin hydrogel barriers," Proc. Natl. Acad. Sci. 91:5967–5971 (1994).

Hubbell, "Hydrogel systems for barriers and local drug delivery in the control of wound healing," Journal of Controlled Release 39:305–313 (1996).

Hubbel, "Biomaterials in Tissue Engineering," Biotechnology 13:565–576 (1995).

Johnson et al., "A month–long effect from a single injection of microencapsulated human growth hormone," Nature Medicine 2(7):795–799 (1996).

Johnson et al., "The Stabilization and Encapsulation of Human Growth Hormone into Biodegradable Microspheres," Pharmaceutical Research 14(6):730–735 (1997).

Jørgensen et al., "Pulsatile Versus Continuous Intravenous Administration Growth Hormone (GH) in GH–Deficient Patients: Effects on Circulating Insulin–Like Growth Factor–I and Metabolic Indices," Journal of Clinical Endocrinology and Metabolism 70(6):1616–1623 (1990).

Krishnamurthy et al., "Stability of Proteins during Manufacture and Release from Biodegradable Polymers" BioPharm, pp. 32–35, Jan. 1998.

Langer, "New Methods of Drug Delivery," Science 249:1527–1533 (1990).

Laursen et al., "Continuous Infusion Versus Daily Injections of Growth Hormone (GH) for 4 Weeks in GH–Deficient Patients," Journal of Clinical Endocrinology and Metabolism 80(8):2410–2417 (1995).

Lee et al., "In Vivo Characterization of Sustained–Release Formulations of Human Growth Hormone," The Journal of Pharmacology and Experimental Therapeutics 281(3):1431–1439 (1997).

Ron et al., "Controlled release of polypeptides from polyanhydrides," Proc. Natl. Acad. Sci. USA 90:4176–4180 (1993).

West et al., "Photopolymerized hydrogel materials for drug delivery applications," Reactive Polymers 25:139–147 (1995).

Sawhney et al., "Bioerodible Hydrogels Based on Photopolymerized Poly(ethylene glycol)–co–poly($\alpha$–hydroxy acid) Diacrylate Macromers," Macromolecules 26(4):581–587 (1993).

BIODEGRADABLE MACROMERS FOR THE CONTROLLED RELEASE OF BIOLOGICALLY ACTIVE SUBSTANCES

CROSS REFERENCE TO APPLICATIONS

This application claims priority from U.S. Ser. No. 60/053,029, filed Jul. 18, 1997, entitled "Biodegradable Hydrogels for Drug Delivery," having as inventor Stephen C. Rowe.

BACKGROUND OF THE INVENTION

The invention relates to methods for administering biologically active substances, and biodegradable compositions for administering these substances.

The rapid advances in the fields of genetic engineering and biotechnology have led to the development of an increasing number of proteins and peptides that are useful as pharmaceutical agents. The development of methods for administering these new pharmaceutical agents is thus gaining increasing importance. In particular, the local or systemic administration of biologically active substances, such as proteins, is a current concern.

The delivery of proteins can be complicated, as proteins will degrade in many of the carriers that have traditionally been used for the administration of small molecules. In many cases, the active forms of proteins are difficult to formulate in biodegradable polymers. Synthetic materials, such as biodegradable hydrogels, can be used to deliver proteins. In many methods, however, the delivery of the protein to the systemic and local circulation is relatively rapid, and is determined primarily by the rate of dissolution of the protein particles. These methods can be of limited utility, as drug release can occur in an initial "burst" rather than at a sustained, controlled rate.

SUMMARY OF THE INVENTION

In a first aspect, the invention features a method for delivering a biologically active substance including the steps of: (a) combining the active substance with a macromer; (b) forming a mixture of the combination formed in step (a); (c) polymerizing the mixture to form articles; and (d) administering the articles, or a portion thereof, to a mammal, where step (c) takes place in the absence of a polymerizable monovinyl monomer.

In a second aspect, the invention features a method for delivering a biologically active substance including the steps of: (a) combining the active substance with a macromer; (b) forming a mixture of the combination formed in step (a); (c) polymerizing the mixture to form articles; and (d) administering the articles, or a portion thereof, to a mammal, where step (c) takes place in the absence of a water soluble polymerizable monovinyl monomer.

In a third aspect, the invention features a method for delivering a biologically active substance including the steps of: (a) combining the active substance with a macromer; (b) forming a mixture of the combination formed in step (a); (c) polymerizing the mixture to form articles; and (d) administering the articles, or a portion thereof, to a mammal, where step (c) takes place in the absence of a vinyl pyrrolidone monomer. The invention also features compositions formed by these methods.

In a fourth aspect, the invention features a method for delivering a biologically active substance including the steps of: (a) combining the active substance with a macromer; (b) forming a mixture of the combination formed in step (a); (c) polymerizing the mixture to form articles; and (d) administering the articles, or a portion thereof, to a mammal, where the articles release at least 80% of the active substance at a time 2.5 times greater than $t_{50}$.

In a fifth aspect, the invention features a method for delivering a biologically active substance including the steps of: (a) combining the active substance with a macromer; (b) forming a mixture of the combination formed in step (a); (c) polymerizing the mixture to form articles; and (d) administering the articles, or a portion thereof, to a mammal, where the articles release a therapeutic dose of the active substance for a period of time at least 2.5 times greater than $t_{50}$.

In a sixth aspect, the invention features a composition for delivering a biologically active substance, the composition including particles including a hydrogel and a biologically active substance, where the release kinetics of the particles are independent of particle size, where the particles have a mass mean diameter of about 50 nm to about 1 mm.

In a seventh aspect, the invention features a method for making articles for the controlled release of a biologically active substance including the steps of: (a) combining the active substance with a biodegradable, polymerizable macromer, the macromer including at least one water soluble region, at least one degradable region which is hydrolyzable under in vivo conditions, and polymerizable end groups having the capacity to form additional covalent bonds resulting in macromer polymerization, where the polymerizable end groups are separated by at least one degradable region, in the presence of an initiator; (b) polymerizing the macromer in the absence of light to form a hydrogel and to incorporate the active substance into the hydrogel; and (c) forming the hydrogel into articles capable of controlled release of the active substance. The initiator may be a radical initiator or an ionic initiator.

In an eighth aspect, the invention features a method for making a polymerized hydrogel, the method including the steps of: (a) combining a hydrophobic, water insoluble macromer, an initiator, and water; (b) allowing the macromer to swell; (c) mixing the macromer to form a homogenous mixture; and (d) polymerizing the macromer to form a hydrogel. Preferably, the method further includes adding a biologically active substance to the mixture before step (d).

In a ninth aspect, the invention features a method for making a polymerized hydrogel including the steps of: (a) combining a hydrophilic macromer and a hydrophobic, water insoluble macromer; (b) heating and stirring the combination formed in step (a) to form a homogenous mixture; (c) cooling the mixture to room temperature (d) adding water and an initiator to the mixture and allowing the mixture to swell; and (e) polymerizing the macromer to form a hydrogel. Preferably, the method further includes adding a biologically active substance to the mixture before step (e).

In a tenth aspect, the invention features a method for delivering a protein including the steps of: (a) combining the protein with a polymerizable hydrophilic polymer; (b) forming a mixture of the combination formed in step (a); (c) polymerizing the mixture to form articles; and (d) administering the articles, or a portion thereof, to a mammal, where the protein remains intact, and where at least 70% of the protein is released from the articles.

In an eleventh aspect, the invention features a method for delivering a biologically active substance, the method including the steps of: (a) combining the active substance with a biodegradable, polymerizable macromer in an aqueous solution, in the presence of a free radical initiator; (b) dispersing the solution to form fine droplets including the macromer and the biologically active substance; (c) polymerizing the macromer in the droplets, thereby forming hydrogel particles having the biologically active substance incorporated therein, where the particles are capable of controlled release of the biologically active agent; and (d) administering the articles, or a portion thereof, to a mammal, where step (c) takes place in the absence of a vinyl pyrrolidone monomer. Preferably, at least 80% of the particles have a particle size of smaller than about 5 µm.

In a twelfth aspect, the invention features a composition including a biologically active substance enclosed within a biodegradable, polymerizable macromer, the macromer including at least one water soluble region, at least one degradable region which is hydrolyzable under in vivo conditions, and polymerizable end groups having the capacity to form additional covalent bonds resulting in macromer polymerization, where the polymerizable end groups are separated by at least one degradable region, where the composition contains at least 5% by weight of the active substance.

In a thirteenth aspect, the invention features an insoluble macromer including at least one water soluble region, at least one degradable region which is hydrolyzable under in vivo conditions, and polymerizable end groups having the capacity to form additional covalent bonds resulting in macromer polymerization, where the polymerizable end groups are separated by at least one degradable region.

In a fourteenth aspect, the invention features composition for the sustained delivery of a protein, where the composition includes an insoluble macromer with at least one water soluble region, at least one degradable region which is hydrolyzable under in vivo conditions, and polymerizable end groups having the capacity to form additional covalent bonds resulting in macromer polymerization, where the polymerizable end groups are separated by at least one degradable region.

In a fifteenth aspect, the invention features a macromer including at least one water soluble region, at least one degradable region which is hydrolyzable under in vivo conditions, and polymerizable end groups having the capacity to form additional covalent bonds resulting in macromer polymerization, where the polymerizable end groups are separated by at least one degradable region, where the degradable region consists essentially of poly(trimethylene carbonate).

In a sixteenth aspect, the invention features a composition for the subcutaneous administration of LHRH, where the composition includes a core of poly(ethylene glycol) having a molecular weight of about 1000 daltons, and a degradable region consisting of poly(caprolactone), where the composition is capable of delivering a therapeutic dose of LHRH for more than 30 days.

In a seventeenth aspect, the invention features a composition comprising glucacon like peptide-1 and a macromer that includes at least one water soluble region, at least one degradable region which is hydrolyzable under in vivo conditions, and polymerizable end groups having the capacity to form additional covalent bonds resulting in macromer polymerization, where the polymerizable end groups are separated by at least one degradable region.

In an eighteenth aspect, the invention features a hydrogel composition for the sustained release of a biologically active substance, where the composition includes particles having a tap density of less than 0.4 g/cm$^3$, where at least 50% of the particles have a mass mean diameter of less than about 5 µm, and where the composition is formulated for pulmonary administration.

In a nineteenth aspect, the invention features a composition for the sustained release of a biologically active substance, where the composition includes particles having a tap density of more than 0.4 g/cm$^3$.

In the aspects of the invention described above, preferred embodiments are as follows. The time at which 10% of the releasable active substance is released is greater than 1/10 of $t_{50}$. Articles and macromer compositions include at least 2.5% active substance by weight, and preferably includes at least 5%, 10%, 25%, or 40% active substance by weight. Macromers include: (a) a water soluble region forming a central core; (b) at least two degradable regions attached to the core; and (c) at least two polymerizable end groups, where the polymerizable end groups are attached to the degradable regions.

The water soluble region includes a polymer selected from the group consisting of poly(ethylene glycol), poly (ethylene oxide), poly(vinyl alcohol), poly (vinylpyrrolidone), poly(ethyloxazoline), poly(ethylene oxide)-co-poly(propylene oxide) block copolymers, polysaccharides, carbohydrates, proteins, and combinations thereof. The water soluble region may include at least 2 arms.

The degradable region includes a polymer selected from the group consisting of poly(α-hydroxy acids), poly (lactones), poly(amino acids), poly(anhydrides), poly (orthoesters), poly(orthocarbonates) and poly (phosphoesters). For example, the degradable region may include poly(trimethylene carbonate) or poly(caprolactone). Alternatively, the degradable region may contain a poly(α-hydroxy acid) selected from the group consisting of poly (glycolic acid), poly(DL-lactic acid) and poly(L-lactic acid). The degradable region may alternatively include a poly (lactone) selected from the group consisting of poly(∈-caprolactone), poly(δ-valerolactone), and poly(γ-butyrolactone). The degradable region may include a copolymer of at least two different monomers or a blend of at least two different monomers.

The polymerizable end groups contain a carbon-carbon double bond capable of polymerizing the macromers.

The articles are administered to the lung of the mammal. Alternatively, the articles are administered intravenously, subcutaneously, intramuscularly, orally, or nasally. Preferably, the articles are administered to humans, and the biologically active substance is preferably a protein.

By "therapeutic dose," when referreing to a biologically active substance, is meant a plasma level between the minimum effective level and the toxic level.

By "release kinetics" is meant the rate at which a drug is released from its device/dosage form.

By "macromer" is meant a polymer with three components: (1) a biocompatible, water soluble region; (2) a biodegradable/hydrolyzable region, and (3) at least two polymerizable regions.

By "intact," when used in the context of a protein or peptide, is meant that the protein or peptide is in its biologically active form, and is not degraded or aggregated.

By "insoluble in water" or "water insoluble" is meant that the solubility of a compound is less than 1 g/100 ml in aqueous solution or in aqueous solution containing up to 5% of an organic solvent, such as dimethylsulfoxide.

The methods and compositions of the invention provide for the controlled release of relatively large quantities of biologically active agents, such as proteins. The macromers used to deliver the proteins both protect the proteins from degrading and also allow for adjusting the release rate of the proteins. Proteins can be delivered over a period of hours, or over a period of months. In addition, the methods and compositions of the invention provide a relatively constant dose of the active substance, rather than a burst of the substance.

DETAILED DESCRIPTION

Figure 1:
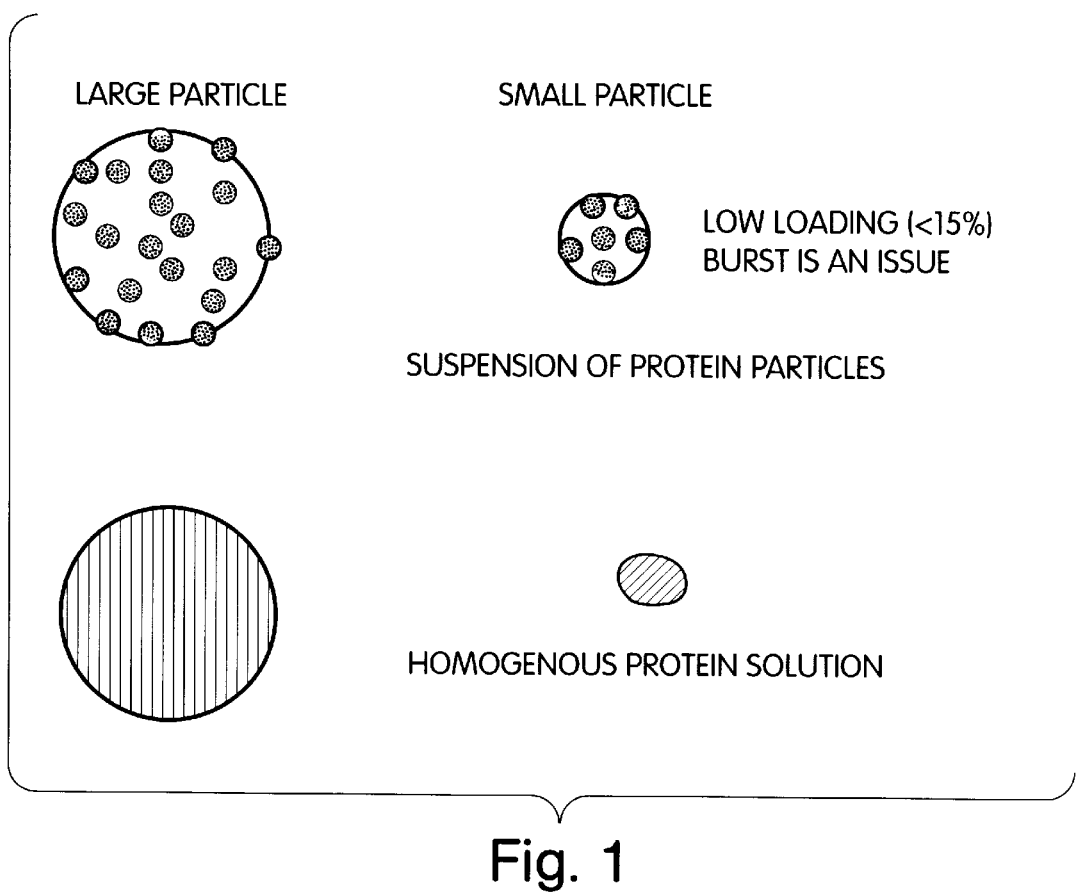
FIG. 1A is a diagram showing particles in which protein particles are unevenly dispersed in the carrier medium.
FIG. 1B is a diagram showing particles in which protein particles are evenly dispersed in the carrier medium.

The invention provides methods and compositions for the administration of biologically active substances. These methods and compositions provide for the controlled, sustained delivery of relatively large quantities of these substances.

In one embodiment, a biologically active substance is combined with a biodegradable, polymerizable macromer in the presence of a polymerization initiator. The macromer is polymerized to form a hydrogel and to incorporate the substance within the resulting hydrogel. The resulting hydrogel, containing the active substance, is formed into articles capable of controlled release of the substance.

Macromers

The macromers of the invention have at least one water-soluble region, at least one degradable (e.g., hydrolyzable) region, and at least one polymerizable region. The macromers may be water-soluble or water insoluble. These macromers are polymerized to form hydrogels, which are useful for delivering incorporated substances at a controlled rate. An important aspect of the macromers is that the polymerizable regions are separated by at least one degradable region. This separation facilitates uniform degradation in vivo.

The ratio between the water-soluble region and the hydrolyzable region of the macromer determines many of the general properties of the macromer. For example, the water solubility of the macromers can be controlled by varying the percentage of the macromer that consists of hydrophobic degradable groups.

There are several variations of these macromers. For example, the polymerizable regions can be attached directly to the degradable regions; alternatively, they can be attached indirectly via water-soluble, nondegradable regions, with the polymerizable regions separated by a degradable region. For example, if the macromer contains a single water-soluble region coupled to a degradable region, one polymerizable region can be attached to the water-soluble region, and the other to the degradable region.

In another embodiment, the water-soluble region forms the central core of the macromer and has at least two degradable regions attached to it. At least two polymerizable regions are attached to the degradable regions so that, upon degradation, the polymerizable regions, particularly in the polymerized gel form, are separated. Alternatively, if the central core of the macromer is formed by a degradable region, at least two water soluble regions can be attached to the core, and polymerizable regions attached to each water soluble region.

In still another embodiment, the macromer has a water-soluble backbone region, with a degradable region attached to the macromer backbone. At least two polymerizable regions are attached to the degradable regions, such that they are separated upon degradation, resulting in gel product dissolution. In a further embodiment, the macromer backbone is formed of a degradable backbone having water-soluble regions as branches or grafts attached to the degradable backbone. Two or more polymerizable regions are attached to the water soluble branches or grafts.

In another variation, the backbone may have multiple arms; e.g., it may be star-shaped or comb-shaped. The backbone may include a water-soluble region, a biodegradable region, or a water-soluble, biodegradable region. The polymerizable regions are attached to this backbone. Again, the polymerizable regions must be separated at some point by a degradable region.

Throughout the specification, the following abbreviations are sometimes used to describe the specific macromers of the invention. In two particular examples, a macromer having a water soluble region consisting of poly(ethylene glycol) with a molecular weight of 4000 daltons, with 5 lactate groups on either side of this region, capped on either side with acrylate groups, is referred to as "4KL5." Similarly, a macromer having a water soluble region consisting of poly(ethylene glycol with a molecular weight of 3,400 daltons, with 6 caprolactone groups on either side of this region, capped on either side with acrylate groups, is referred to as "3.4KC6."

Water-Soluble Region

The water soluble region may include poly(ethylene glycol), poly(ethylene oxide), poly(vinyl alcohol), poly (vinylpyrrolidone), poly(ethyloxazoline), poly(ethylene oxide)-co-poly(propylene oxide) block copolymers, polysaccharides, carbohydrates, or proteins, or combinations thereof.

The macromer preferably comprises a water soluble core region comprising poly(ethylene glycol) (PEG), as PEG has high hydrophilicity and water solubility, as well as good biocompatibility. The poly(ethylene glycol) region preferably has a molecular weight of about 400 to about 40,000 Da, and more preferably has a molecular weight of about 1,000 to about 30,000 Da, about 1,000 to about 20,000 Da, or about 2,000 to about 10,000 Da.

Degradable Region

The degradable region may contain, for example, poly($\alpha$-hydroxy acids), poly(lactones), poly(amino acids), poly (anhydrides), poly(orthoesters), poly(orthocarbonates) or poly(phosphoesters), or blends or copolymers of these polymers.

Exemplary poly($\alpha$-hydroxy acids) include poly(glycolic acid), poly(DL-lactic acid) and poly(L-lactic acid). Exemplary poly(lactones) include poly($\epsilon$-caprolactone), poly($\delta$-valerolactone), poly($\gamma$-butyrolactone), poly(1,5-dioxepan-2-one), and poly(trimethylene carbonate).

Examples of copolymers include a copolymer of caprolactone and glycolic acid; and a copolymer of caprolactone and lactic acid.

Polymerizable Region

The polymerizable regions preferably contain carbon—carbon double bonds capable of polymerizing the macromers. The choice of appropriate polymerizable group permits rapid polymerization and gelation. Polymerizable regions containing acrylates are preferred because they can be polymerized using several initiating systems, as discussed below. Examples of acrylates include acrylate, methacrylate, and methyl methacrylate.

Polymerization Step

The macromers are polymerized using polymerization initiators under the influence of long wavelength ultraviolet light, visible light, thermal energy, or a redox system. The polymerization can be conducted at room temperature or at lower temperatures, for example, temperatures less than 20° C. During polymerization, substances such as proteins are physically incorporated into the resulting polymer network of the gel.

The polymerization may be initiated in situ by light having a wavelength of 320 nm or longer. When the polymerizable region contains acrylate groups, the initiator may be any of a number of suitable dyes, such as xanthine dyes, acridine dyes, thiazine dyes, phenazine dyes, camphorquinone dyes, acetophenone dyes, or eosin dyes with triethanolamine, 2,2-dimethyl-2-phenyl acetophenone, and 2-methoxy-2-phenyl acetophenone.

The polymerization may also take place in the absence of light. For example, the polymerization can be initiated with a redox system, as described in more detail in the Examples. In some cases it is advantageous to be able to polymerize using the redox system of the invention, as radical initiator production occurs at reasonable rates over a wide range of temperatures.

Initiators that can be used in the redox system include, without limitation, peroxides such as acetyl, benzoyl, cumyl and t-butyl; hydroperoxides such as t-butyl and cumyl, peresters such as t-butyl perbenzoate; acyl alkylsulfonyl peroxides, dialkyl peroxydicarbonates, diperoxyketals, ketone peroxide, azo compounds such as 2,2'-azo(bis) isobutyronitrile (AIBN), disulfides and tetrazenes.

Properties of the Macromers

The articles of the invention are biodegradable. Biodegradation occurs at the linkages within the extension oligomers and results in fragments which are non-toxic and easily removed from the body and/or are normal, safe chemical intermediates in the body. These materials are particularly useful for the delivery of hydrophilic materials, since the water soluble regions of the polymer allow water to access the materials trapped within the polymer.

More importantly, the articles are capable of degrading under in vivo conditions at rates which permit the controlled release of incorporated substances. Release may occur by diffusion of the material from the polymer prior to degradation and/or by diffusion of the material from the polymer as it degrades. Degradation of the polymer facilitates eventual controlled release of free macromolecules in vivo by gradual hydrolysis of the terminal ester linkages. The burst effects that are sometimes associated with other release systems are thus avoided in a range of formulations.

The rate of release depends, in part, on the composition of the water soluble region, such as the molecular weight of the components in the water soluble region. The rate of release of the biologically active agent also may be dependent upon the degree of polymerization of the macromer, as well as on other factors.

The rate of release of the substance also depends on the rate of degradation of the degradable region of the macromer. For example, glycolic esters lead to very rapid degradation, lactic esters to somewhat slower degradation, and caprolactic esters to very slow degradation. When the degradable region consists of polyglycolic acid, the release period is less than one week. When the degradable region consists of poly(lactic acid), the release period is about one week. When the degradable region consists of a copolymer of caprolactone and lactic acid or a copolymer of trimethylene carbonate and lactic acid, the release period is two to four weeks. When the degradable region consists of poly (trimethylene carbonate) or a copolymer of caprolactone and trimethylene carbonate, the release period is about three to eight weeks. When the degradable region consists of poly (trimethylene carbonate)or poly(caprolactone), the release period is longer than about five weeks.

The precise rate of release can be further modified by altering the ratio of hydrophilic and hydrophobic components. For example, a very soluble macromer will yield, after polymerizing, a hydrophilic gel; hydrophilic hydrogels have been shown to degrade more rapidly than hydrophobic ones. A blend of a hydrophilic macromer (e.g., 4KL5) with a hydrophobic water insoluble macromer (3.4KC6) is used to form a polymerized hydrogel. This hydrogel will have a release rate that is in between the release rate of a hydrogel containing only lactic acid and a hydrogel containing only caprolactone. A macromer in which the degradable region is a copolymer of caprolactone and lactic acid will also have a release rate that is in between the release rate of a hydrogel containing only lactic acid and a hydrogel containing only caprolactone as the primary degradable group.

In addition, the rate of release of a given article depends on the quantity of the loaded substance, as a percent of the final product formulation; the solubility of the active substance; the hydrophilicity of the active substance (hydrophilic active substances will generally be released faster than hydrophobic ones); and, in the case of suspensions, particle size. By adjusting the factors discussed above, degradation and controlled release may be varied over very wide ranges. For example, release may be designed to occur over hours, days or months.

As shown in FIG. 1, the methods of the invention can produce particles that behave as homogenous drug delivery systems. Because of the homogenous nature of the articles of the invention, there is no initial burst of released substance. In addition, the uniform consistency makes it possible to incorporate relatively high amounts of protein, while still minimizing the burst release.

Generally, water-soluble substances will yield homogenous systems when incorporated into the macromers of the invention. Substances that do not solubilize in water within the time it takes to form the macromers of the invention will yield heterogenous systems. The amount of burst in the heterogenous systems can be minimized by using a particulate suspension with small particles.

Figure 2:
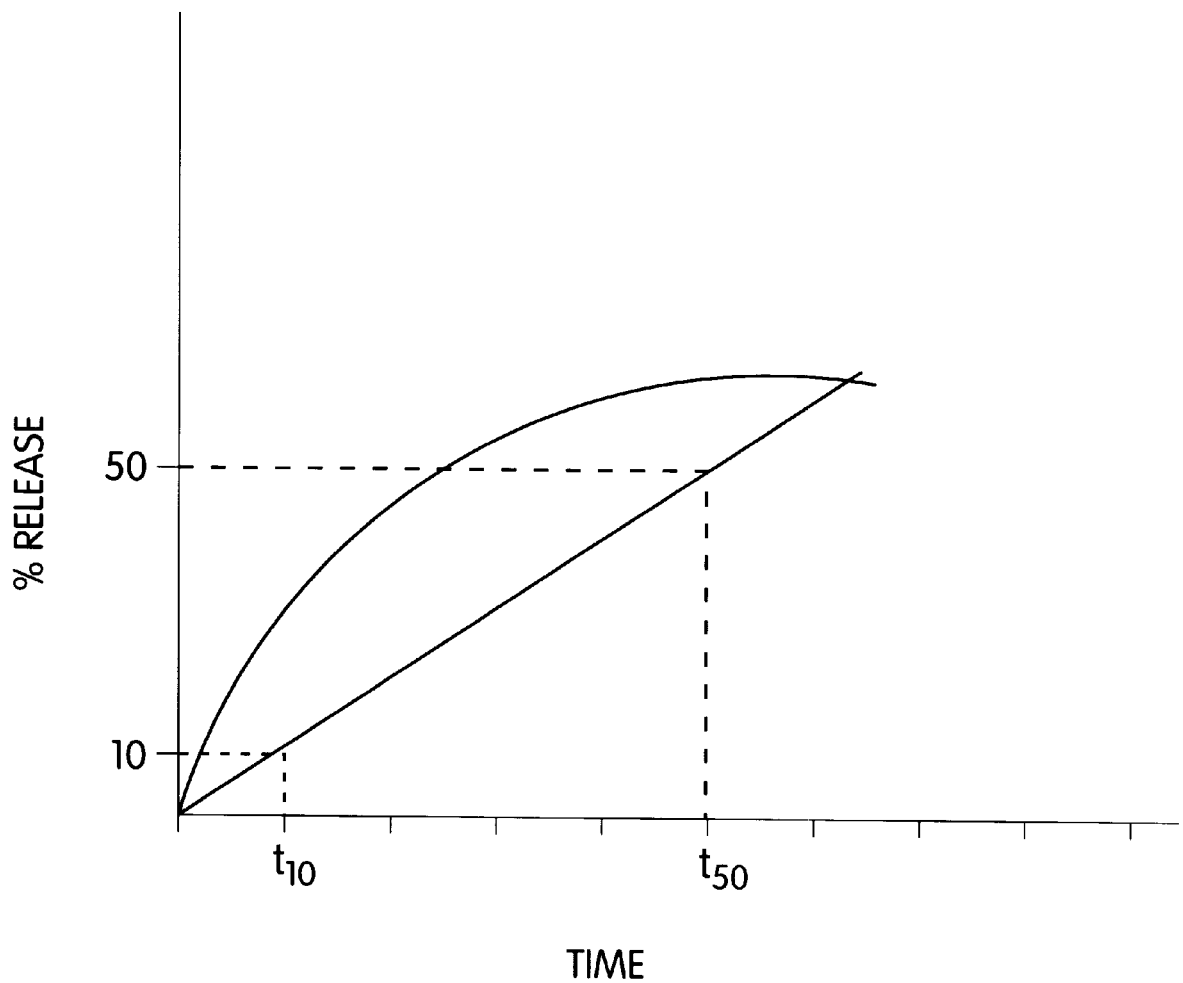
FIG. 2 is a graph showing the release profile of a substance from a macromer composition.

A release profile of a substance is shown in FIG. 2. The horizontal axis shows the time after administration, and the vertical axis represents the amount of material released. As shown in FIG. 2, time $t_{50}$ is the time at which 50% of the releasable material has been released. Time $t_{10}$) is, correspondingly, the time at which 10% of the releasable material has been released. The amount of releasable active substance is the amount that is released from an article in a period of time 10 times greater than the period of time it takes for 10% of the incorporated active substance to be released.

When the release curve is perfectly linear, $t_{10} = \frac{1}{5}$ of $t_{50}$. When there is an initial burst, $t_{10}$ is much less than $\frac{1}{5}$ of $t_{50}$. In the methods and compositions of the invention, $t_{10}$ is preferably greater than $\frac{1}{10}$ of $t_{50}$. In other words, there is no, or very little, initial "burst" of release of the material.

The invention also features insoluble macromers. These macromers contain at least one water-soluble region, at least one degradable (e.g., hydrolyzable) region, and at least one polymerizable region. The degradable region contains polymers of glycolic acid, lactic acid, or caprolactone, trimethylene carbonate, or blends or copolymers thereof. The degradable region must be water insoluble. For example, a macromer having a degradable region containing 15–20 lactide units can be prepared; this macromer will provide a relatively fast release rate. A macromer with a degradable region containing 6 caprolactone units will provide a relatively slow release rate. A macromer with a degradable region containing a copolymer of 6 caprolactone units, 4 lactide units, and 4 glycolide units will provide a fast release rate, and a macromer with a degradable region containing a copolymer of 3 lactide units and 7 trimethylene carbonate units will provide an intermediate release rate.

The water soluble region of these macromers is preferably PEG. The water soluble region can have multiple arms; for example, it may be star-shaped or comb-shaped. The water soluble region preferably has 4, 6, or 8 arms and a molecular weight of 10,000 to 40,000 daltons.

High Load Characteristics

Therapeutic agents may be readily incorporated in high yield into the articles described herein. For example, articles may be prepared containing at least 2.5% active substance by weight. Preferably, the articles contain at least 5, 10, 25, or 40% by weight.

The amount of loaded active substance may be measured by dissolving pieces of the articles into an appropriate solvent and assaying the amount of active substance present by means available in the art, such as spectrophotometry.

Shaping of Articles

The articles formed using the procedures described above may be formed in any shape desired. For example, the articles may be shaped to fit into a specific body cavity. They may also be formed into thin, flat disks or microspheres. Alternatively, the articles may be shaped, then processed into the desired shape before use, or ground into fine particles. The desired shape of the article will depend on the specific application.

Particles may be prepared using techniques known in the art, including single and double emulsion solvent evaporation, spray drying, and solvent extraction. As used herein, the term "particles" includes, but is not limited to, microspheres. In a microsphere, a therapeutic or other agent substantially is dispersed throughout the particle. The particles may have a smooth or irregular surface, and may be solid or porous. Methods for making microspheres are described in the literature, for example, in Mathiowitz and Langer, *J. Controlled Release* 5:13–22 (1987); Mathiowitz et al., *Reactive Polymers* 6:275–283 (1987); Mathiowitz et al., *J. Appl. Polymer Sci.* 35:755–774 (1988); Mathiowitz et al., *Scanning Microscopy* 4:329–340 (1990); Mathiowitz et al., *J. Appl. Polymer Sci.*, 45:125–134 (1992); and Benita et al., *J. Pharm. Sci.* 73:1721–1724 (1984).

In solvent evaporation, described for example, in Mathiowitz, et al., (1990), Benita et al. (1984), and U.S. Pat. No. 4,272,398, a polymer is dissolved in a volatile organic solvent, such as methylene chloride. An agent to be incorporated, either in soluble form or dispersed as fine particles, is optionally added to the polymer solution, and the mixture is suspended in an aqueous phase that contains a surface active agent such as poly(vinyl alcohol). The resulting emulsion is stirred until most of the organic solvent evaporates, leaving solid microspheres, which may be washed with water and dried overnight in a lyophilizer.

In solvent removal, a therapeutic or diagnostic agent is dispersed or dissolved in a solution of a selected polymer in a volatile organic solvent such as methylene chloride. The mixture can then be suspended in oil, such as silicon oil, by stirring, to form an emulsion. As the solvent diffuses into the oil phase, the emulsion droplets harden into solid polymer microspheres.

Processes for preparing ultrafine particles of biological molecules by atomizing liquid solutions of the macromolecules, drying the droplets formed in the atomization step, and collecting the particles are described in PCT WO 97/41833.

Spray drying is implemented by passing a homogenous mixture of a substance, such as a therapeutic agent, and the polymerizable macromer used to form the hydrogel through a nozzle, spinning disk or equivalent device to atomize the mixture to form fine droplets. The substance and the polymerizable macromer may be provided in a solution or suspension, such as an aqueous solution. The fine droplets are exposed to light to cause polymerization of the macromer and formation of the hydrogel droplets incorporating the substance.

In another embodiment, hydrogel particles are prepared by a water-in-oil emulsion process, wherein the polymerizable macromers and the substance to be incorporated are suspended in a water-in-oil emulsion and exposed to light to polymeriz and polymerize the macromers to form hydrogel particles incorporating the substance, such as a biologically active agent. Typically, polymerization may be conducted at room temperature.

The microspheres prepared using the techniques described above are freeze dried, so they have a long shelf life (without biodegradation) and the drug remains biologically active. Prior to use for injectable formulations, the microspheres are reconstituted in a suitable solution, such as saline or other liquids. For pulmonary delivery, the freeze dried or reconstituted particles may be used.

Biologically Active Substances

Biologically active substances that can be incorporated into the compositions of the invention include therapeutic, diagnostic and prophylactic agents. They can be naturally occurring compounds, synthetic organic compounds, or inorganic compounds. Substances that can be incorporated into the articles of the invention include proteins, peptides, carbohydrates, inorganic materials, antibiotics, antineoplastic agents, local anesthetics, antiangiogenic agents, vasoactive agents, anticoagulants, immunomodulators, cytotoxic agents, antiviral agents, antibodies, neurotransmitters, psychoactive drugs, oligonucleotides, lipids, cells, tissues, tissue or cell aggregates, and combinations thereof.

Exemplary therapeutic agents include calcitonin, granulocyte macrophage colony stimulating factor (GMCSF), ciliary neurotrophic factor, parathyroid hormone, and the cystic fibrosis transmembrane regulator gene.

Other specific therapeutic agents include parathyroid hormone-related peptide, somatostatin, testosterone, progesterone, estradiol, nicotine, fentanyl, norethisterone, clonidine, scopolomine, salicylate, salmeterol, formeterol, albeterol, and valium.

Drugs for the treatment of pneumonia may be used, including pentamidine isethiouate. Drugs for the treatment of pulmonary conditions, such as asthma, may be used, including albuterol sulfate, β-agonists, metaproterenol sulfate, beclomethasone diprepionate, triamcinolone acetamide, budesonide acetonide, ipratropium bromide, flunisolide, cromolyn sodium, ergotamine tartrate, and protein or peptide drugs such as TNF antagonists or interleukin antagonists.

Other therapeutic agents include cancer chemotherapeutic agents, such as cytokines, lymphokines, and DNA, and vaccines, such as attenuated influenza virus. Nucleic acids that can be incorporated include genes, cDNAs encoding proteins, expression vectors, antisense molecules that bind to complementary nucleic acid sequences to inhibit transcription or translation, and ribozymes. For example, genes for the treatment of diseases such as cystic fibrosis can be administered. Polysaccharides, such as heparin, can also be administered.

Other therapeutic agents include tissue plasminogen activator (t-Pa), superoxide dismutase, catalase luteinizing hormone releasing hormone (LHRH) antagonists, IL-11 platelet factor, IL-4 receptor, enbrel, IL-1 receptor antagonists, TNF receptor fusion proteins, megakaryocyte growth and development factor (MGDF), stemgen, anti-HER-2 and anti-VEGF humanized monoclonal antibody, anti-Tac antibody, GLP-1 amylin, and GLP-1 amylin analogues.

Additional therapeutic agents include atrial natriuretic factor, atrial natriuretic peptide, beta-human chorionic gonadotropin, basic fibroblast growth factor, bovine growth hormone, bone morphogenetic protein, B cell stimulating factor-1, B cell stimulating factor-2, bovine somatotropin, carcinobreaking factor, cartilage induction factor, corticotropin releasing factor, colony stimulating factor, differentiating factor-1, endothelial cell growth factor, erythroid differentiation factor, elongation factor 1-alpha, epidermal growth factor, erythropoietin, fibroblast growth factor, follicle stimulating hormone, granulocyte colony stimulating factor, glial fibrallary acidic protein, growth hormone releasing factor, human alpha-1 antitrypsin, human atrial natriuretic factor, human chorionic gonadotropin, human growth hormone, human leukemia inhibitory factor, hemopoictin-1, hepatocyte growth factor, human transforming growth factor, human thyroid-stimulating hormone, interferon, immunoglobulin A, immunoglobulin D, immunoglobulin E, insulin-like growth factor-1, insulin-like growth factor-II, immunoglobulin G, immunoglobulin M, interleukin-1, interleukin-2, interleukin-3, interleukin-4, interleukin-5, interleukin-6, kidney plasminogen activator, lectin cell adhesion molecule, luteinizing hormone, leukemia inhibitor factor, monoclonal antibody, macrophage activating factor, macrophage cytotoxic factor, macrophage colony stimulating factor, megakaryocyte colony stimulating factor, A tumor necrosis factor, macrophage inhibitory factor, Mullerian inhibiting substance, mcgakaryocyte stimulating factor, melanocyte stimulating factor, neutrophil chematactic factor, nerve growth factor, novel plasminogen activator, nonsteroidal anti-inflammatory drug, osteogenic factor extract, antitumor lymphokine, prostate-specific antigen, anti-platelet activating factor, plasminogen activator inhibitor, platelet-derived growth factor, platelet-derived wound healing formula, plasmatic human interleukin inducing protein, tumor angiogenesis factor, tissue control factor, T cell growth factor, T cell modulatory peptide, transforming growth factor, tumor growth inhibitor, tumor inhibiting factor, tissue inhibitor of metalloproteinases, tumor necrosis factor, tissue plasminogen activator, thrombopoietin, thyroid stimulating hormone, urokinase-plasminogen activator, vascular endothelial growth factor, and vasoactive intestinal peptide.

Exemplary diagnostic agents include gases and other commercially available imaging agents that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper and chromium chelates. Examples of materials useful for CAT and X-rays include iodine based materials.

A preferred biologically active substance is a protein. Proteins are defined as consisting of 100 amino acid residues or more; peptides are less than 100 amino acid residues. Unless otherwise stated, the term protein refers to both proteins and peptides. The proteins may be produced, for example, by isolation from natural sources or recombinantly. Examples include insulin and other hormones, including growth hormones, such as human growth hormone and bovine growth hormone. Other exemplary proteins include Factor VIII, Factor IX, Factor VIIa, and anti-inflammatory agents, such as interleukins, including interleukin-4, NSAIDs or corticosteriods. Other exemplary proteins include enzymes, such as DNase and proteases. Other proteins include cytokines, interferons, including interferon alpha and interferon beta, poetins, colony-stimulating factors, growth factors, ceredase, gibberellins, auxins and vitamins, and fragments thereof. Exemplary growth factors include vascular endothelial growth factor (VEGF), endothelial cell growth factor (ECGF), basic fibroblast growth factor (bFGF), and platelet derived growth factor (PDGF).

Proteins are stable in the hydrogels of the invention. For example, many of the proteins are protected from dimerization or aggregation, as discussed below in the Examples. The enzymatic degradation of proteins or peptides can be further minimized by co-incorporating peptidase-inhibitors.

Routes of Administration

Inhalation

The use of the hydrogel particles of the invention can enhance the delivery of drugs to the lung. Administration to the lung provides for the delivery of drugs that can be transported across the lung tissue barriers and into circulation, as described in U.S. Provisional Patent Application Serial No. 60/053,029, filed Jul. 18, 1997.

A problem with the delivery of active substances to the lung is that pulmonary macrophages can take up the materials, thus preventing the material from entering into systemic and local circulation. Uptake occurs when proteins adsorbed to the particles' surfaces bind with receptors on the surfaces of the macrophages. To prevent uptake, the invention provides nonionic hydrogels, e.g., formed with polymers based on polyethylene glycol. These hydrogels adsorb low levels of proteins and thus bind poorly to cell surfaces. Anionic hydrogels, e.g., formed with polyacrylic acid, also adsorb relatively low levels of proteins and thus bind poorly to cell surfaces.

In a further embodiment, biocompatible microcapsules may be formed and the surface provided with water soluble non-ionic polymers such as polyethylene oxide (PEO), to create resistance to cell adhesion, as described in U.S. Pat. No. 5,380,536.

The size and density of the particles can also be selected to maximize the quantity of active substance that is delivered to the lung. For example, the maerophages will not take up large particles as efficiently as they will take up small particles. However, large particles are not delivered to the deep lung as well as small particles are. To overcome these conflicting factors, the invention provides small particles that can swell as they hydrate. The particles are administered to the deep lung as small (i.e., 1–5 μm), dry, or slightly wet, particles; upon hydration, they swell, and therefore become resistant to uptake by the pulmonary macrophages. The swelling can occur when the particles are hydrated from the dry state and when they are hydrated from one state of hydration to another by a change in temperature, pH, salt concentration, or the presence of other solvents, for example, depending upon the chemical and physical nature of the hydrogel polymer.

As used herein, the term "dry" means that the particles of the powder have a moisture content such that the powder is readily dispersible in an inhalation device to form an aerosol. Preferably, the moisture content of the particles is below 10% by weight water, more preferably below about 5%, or optionally below about 2%, or lower.

The density of the particles is expressed in terms of tap density. Tap density is a standard measure of the envelope mass density. The envelope mass density of an isotropic particle is defined as the mass of the particle divided by the minimum sphere envelope volume within which it can be enclosed. The density of particles can be measured using a GeoPyc (Micrometers Instrument Corp., Norcross, Ga.) or a AutoTap (Quantachrome Corp., Boyton Beach, Fla.).

For example, the density of 3.4KL5 particles was determined as follows. 3.4KL5 (1.0025 g), 200 mM TEOA in PBS pH 7 (1.0260 g) and 1000 ppm Eosin (0.1028 g) were combined. 200 mg of this solution was mixed with talc (0.1015 g). The resulting suspension was placed in a 100 μL glass pipet and polymerized by light for 15 seconds (ILC Technology, Inc. Xenon Light Source with Fiber Optics). The rod was pushed out, placed on aluminum foil, and further polymerized for 3.5 minutes. The hardened rod was lyophilized (vacuum 15E-3 mbar, trap temp. −50° C.) for 18 hours. The dry rod (water content <10%) was cut into small pieces, placed in heptane, and minced using a homogenizer (Silverson L4RT-A) at 5,000 rpm to small particles. The wet particles were air-dried, followed by nitrogen gas flow. The particles sizes ranged from 1 μm to 0.5 mm.

1.645 g of these particles was placed in a 10 mL graduated cylinder. The graduated cylinder was mounted on top of Autotap densimeter (Quantachrome). The sample was taped 100 times and the particles' volume was read. The process was repeated until no change in volume was observed. The final volume was 2.8 mL. The tap density of the particles was 1.6435 g/2.8 mL=0.5870 g/mL.

In addition to particles, the polymer may be provided in other shapes suitable for delivery to the deep lung. For example, PEG emulsion microspheres are subjected to high pressure and a vacuum onto a flat plate to form very light very thin layers, for example, having a snow flake consistency, that react differently to fluidic wind forces. The resulting thin flakes can be, e.g., 0.01 μm, 1 μm, or 10 μm thick.

The particles can be administered to the respiratory system alone, or in any appropriate pharmaceutically acceptable excipient, such as a liquid, for example saline, or a powder. Aerosol dosages, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6:273–313, 1990; and in Moren, "Aerosol dosage forms and formulations," in: Aerosols in Medicine. Principles, Diagnosis and Therapy, Moren, et al., Eds., Elsevier, Amsterdam, 1985.

Pulmonary drug delivery may be achieved using devices such as liquid nebulizers, aerosol-based metered dose inhalers, and dry powder dispersion devices. For the use of dry powder dispersion devices, the polymer particle incorporating the therapeutic agent is formulated as a dry powder, for example, by lyophilization or spray-drying. Methods for preparing spray-dried, pharmaceutical-based dry powders including a pharmaceutically acceptable amount of a therapeutic agent and a carrier are described in PCT WO 96/32149.

Examples of drug that can be administered to the lung include, without limitation, insulin, antitrypsin, calcitonin, alpha interferon, beta interferon, GLP-1, and DNAse.

Nasal Delivery

The compositions can also be used to administer compounds nasally. For example, a vaccine containing freeze dried or reconstituted microspheres can be administered nasally.

Intramuscular and Subcutaneous Administration

The articles of the invention can be used to administer microspheres that degrade over several days to 3 months, by intramuscular injection or by subcutaneous injection.

For example, growth hormone can be administered subcutaneously; the hormone leaves the microspheres at the site of injection as they degrade. Growth hormone enters the systemic circulation, where, in turn, it exerts its effects directly, and indirectly through induction of somatomedin production in the liver. For this application, particle sizes of up to 0.5 mm can be used.

In other embodiments, the active agent is a vaccine, such as tetanus vaccine, other proteins or peptides, or more complex immunogens. The vaccine is released over time, from one week to many weeks, resulting in an improved immune response to the vaccine, compared to a bolus injection followed by one or more booster shots with the same total dose of immunogen. Mixtures of different types of microspheres can result in initial and booster shot-type immunization as well.

Intravenous Administration

Hydrogel microspheres that contain a drug useful in treating clotting disorders, such as Factor VIII or Factor IX for hemophilia, can be administered by intravenous injection. The drug is released over days to weeks. A therapeutic level of the drug is maintained that results in a better clinical outcome. In addition, potentially lower total doses of drugs can be administered, with a corresponding economic benefit. These approaches help promote patient compliance.

In the case of intravenous injection, it is important to formulate the microspheres in acceptable agents so the microspheres do not aggregate and clog blood vessels. The microspheres must be appropriately sized, so that they don't lodge in capillaries. For this application, particle sizes of 0.2–0.5 μm are preferred.

In a number of inflammatory conditions, as part of the inflammatory process that is mediated by selectin and ICAM expression/binding with neutrophil intravisation, blood vessels become leaky at the site of inflammation. Hydrogel microspheres may be administered; these microspheres will leak out of blood vessels at the site of inflammation, and then release their drug payload locally over a period of time. Disease conditions where this approach may be useful could include, but are not limited to, inflammatory bowel diseases, asthma, rheumatoid arthritis, osteoarthritis, emphysema, and cystic fibrosis (with DNAase as the enzymatic drug).

Hydrogel microspheres that contain cytokines, lymphokines, or other compounds to treat cancer can be administered by intravenous injection. Blood vessels within large solid tumors are generally leaky, and the blood flow within them is often slow. Thus, microspheres could lodge within solid tumors and release their anticancer drug locally, either killing tumor cells directly or by activating the immune system locally. This approach could be used, for example, with compounds such as interleukin 2, where the systemic and local toxicity has been dose limiting and there have been significant side effects.

The microspheres of the invention will be cleared relatively slowly from the circulation. Alternatively, the microspheres can be targeted to exit the circulatory system through leaky blood vessels or through more active targeting mechanisms, e.g., receptor mediated targeting mechanisms.

Oral Administration

In some portions of the gastrointestinal tract, there is relatively good transport of proteins across the intestinal mucosa into the systemic and local circulation. The compositions of the invention, for example, freeze dried microspheres containing protein (with very small particle sizes), can therefore be administered orally in an appropriate enteric formulation that protects the drug-containing microspheres from enzymatic attack and the low pH's found in the upper GI tract. Such an enteric formulation could also be designed using several available technologies to gradually expel drug-containing microspheres as the enteric capsule traverses the gastrointestinal tract. This is described in more detail in provisional application U.S. Ser. No. 60/053,029 and in Mathiowitz et al., Nature 386 (6623): 410–414 (1997). It is anticipated that this approach will have a number of advantages over other approaches for delivering proteins and other molecules, even small molecules, orally. First, PEG and proteins are compatible, so the major manufacturing and stability problems found with other drug delivery approaches can be avoided. Secondly, dried hydrogels are very adhesive to wet tissue. The microparticles will bind well to the GI tract and will be transported into the system via the gastrointestinal circulation or release their contents on the intestinal mucosa; in turn, the drug will enter the systemic and gastrointestinal circulation. Chemical enhancers, or formulations containing compositions that utilize specific and non-specific biological transport mechanisms to facilitate transport across the GI tract into the systemic circulation, can be included as well.

Targeting

Targeting ligands can be attached to the particles via reactive functional groups on the particles. Targeting ligands permit binding interactions of the particle with specific receptor sites, such as those within the lungs or those on endothelial cells specific to different regions in the body's microvasculature. A targeting ligand is selected which specifically or non-specifically binds to particular targets. Exemplary targeting ligands include antibodies and fragments thereof including antibody variable regions, lectins, hormones, or other organic molecules capable of specific binding to receptors on the surfaces of the target cells. Other ligands are described in Science, Vol. 279, 323–324 (1998).

Microspheres can be made with both a drug and a targeting molecule. Double microspheres can also be made, in which the inner sphere contains drug and the outer PEG shell contains the targeting molecule or reagent.

Excipients and Carriers

The particles incorporating a therapeutic agent or diagnostic agent may be provided in combination with one or more pharmaceutically acceptable excipients available in the art, as described, for example, in PCT WO 95/31479. Excipients may be selected that can, in some applications, enhance stability, dispersability, consistency and bulking to ensure uniform pulmonary delivery. The excipient may be, e.g., human serum albumin (HSA), bulking agents such as carbohydrates, amino acids, peptides, pH adjusters or buffers, and salts. Additional excipients include zinc, ascorbic acid, mannitol, sucrose, trehalose, cyclodextrans, polyethylene glycol, and other commonly used pharmaceutical excipients, including those described in The United States Pharmacopeia, published by the United States Pharmacopeia Convention, Inc., 1995 (see, e.g., pp. 2205–2207). Exemplary carbohydrates include monosaccharides, such as galactose, and disaccharides such as lactose. Excipients that stabilize proteins are especially useful.

In some cases, the excipients are used as carriers; i.e., they are used to modulate the release rate of the active substances. For example, mannitol can be used to accelerate or delay release.

There now follow particular examples that describe the preparation of compositions of the invention, and the methods of the invention. These examples are provided for the purpose of illustrating the invention, and should not be construed as limiting.

In some of the following examples a macromer made of a triad ABA block copolymer of acrylate-PLA-PEG-PLA-acrylate was used. The PEG had a MW of 3,400; the poly(lactic acids) on both sides had an average of about five lactate units per side; they are therefore referred to herein as "3.4KL5." When a lower molecular weight PEG, such as 2,000 was used, the resulting macromer is abbreviated as "2KL5."

In other examples an acrylate-PCL-PEG-PCL-acrylate macromer was used. The PEG had a MW of 3,400 and had polycaprolactone on both sides, with an average of about 6 caproyl units per side. The polymer is referred to herein as "3.4KC6."

All animals studies described herein were conducted with the approval of the Institutional Animal Care and Use Committee.

EXAMPLE 1

General Preparation of a Macromer Solution

The protein was weighed out, and the following components were added to the protein: (i) 90 mM TEOA/PBS, pH 8.0; (ii) 35% n-vinyl pyrrolidinone (n-VP); and (iii) 1000 ppm Eosin. The resulting mixture was stirred well using a spatula. The solution was kept in the dark for about 10 minutes, or until the macromer had absorbed all of the solution, or until the solution was homogenous.

Macromer solutions having the following ingredients were prepared.

| Amount Protein | Amount 90 mM TEOA | Amount 35% n-VP | Amount 1000 ppm Eosin | Amount 3.4KL5 | Amount 2KL5 | Total amount |
|---|---|---|---|---|---|---|
| 15 mg | 57 mg | 15 mg | 3 mg | 45 mg | 0 mg | 135 mg |
| 15 mg | 57 mg | 15 mg | 3 mg | 0 mg | 45 mg | 135 mg |

EXAMPLE 2

Preparation of a Hydrogel from a Water Insoluble Macromer 0.5 g of 3.4KC6 was added to a 20-cc scintillation vial. 0.5 mL of 200 mM TEOA, pH 6.95/PBS buffer was added, and the macromer was allowed to swell. The macromer was then mixed until it formed a homogeneous mixture. To this mixture were added 20 µL of 1000 PPM eosin solution in PBS, 10 µL of a 35% solution of n-VP, and 0.0845 g ZnbST.

The resulting solution was placed onto a silanized glass slide. Using pieces of plastic sheets with thicknesses of about 0.4±0.2 mm as spacers, another silanized glass slide was placed on top and held firmly in place using binder clips.

A light source (ILC Technology, Inc. Xenon Light Source with Fiber Optics) was adjusted to about a 5-cm distance for illumination from the light source to the glass slide, using clamps and a stand. Both sides of the disc were illuminated for two minutes each to form an opaque disc.

EXAMPLE 3

Preparation of a Hydrogel from a 50:50 Blend of Water Soluble and Insoluble Macromer 0.56 g 3.4KL5 and 0.56 g were placed in a scintillation vial. The vial was placed in a 52° C. oven; the mixture was sporadically mixed until it formed a homogenous composition. It was then cooled to room temperature. To 0.5 g of the above mixture were added 0.5 mL of 200 mM TEOA and pH 6.95/PBS buffer. The resulting macromer was allowed to swell.

Once swollen, the macromer was mixed until it formed an homogeneous composition with a dough-like consistency. To this composition were added 20 µL 1000-PPM Eosin solution in PBS and 10 µL 35% solution of n-VP and 0.0845 g of ZnbST. The resulting solution was stirred, then placed onto a silanized glass slide. Using pieces of plastic sheets with thicknesses of about 0.4±0.2 mm as spacers, another silanized glass slide was placed on top and held firmly in place using binder clips.

A light source (ILC Technology, Inc. Xenon Light Source with Fiber Optics) was adjusted to about a 5-cm distance. The center of the disc was illuminated; both sides of the disc were illuminated for two minutes each, to form an opaque disc.

EXAMPLE 4

Production of Microspheres Using a REDOX Initiating System 300 mg of 3.4KL5 was dissolved in 1 mL of PBS containing 0.5% ammonium persulfate. 30 mL of silicone oil (100 cp) was degassed with nitrogen. 0.25 mL of the aqueous media containing the macromer was added to the oil and stirred at 2000 rpm using a Silverson homogenizer equipped with ⅝" head. After the combination was mixed thoroughly for 5 minutes, 0.5 mL of tetramethylethylene diamine was added. The resulting emulsion was stirred for 30 minutes. After 30 minutes, 20 mL of heptane was added. The resulting suspension was centrifuged at 2000 rpm for 2 minutes and collected from the bottom of the centrifuge tube. The resulting microspheres were analyzed by light microscopy @400× using phase contrast. The average microsphere size was found to be 2.5 µm.

EXAMPLE 5

Long Term Release of bST

Device Preparation: A blend of a degradable macromer (3.4KL5) and a non-degradable macromer (PEG-diacrylate, MW 3,400) was used. The protein used was ZnbST (Monsanto/Protiva). The protein was loaded at a loading of 20%, based on dry weight. 3 samples were prepared, as follows.

Sample preparation: 20 µL of the bST-precursor solution were prepared, as described in Example 1. The mixture was pipetted using a positive displacement pipette with a silanized glass tip. The solution was placed onto a silanized glass slide. Using pieces of plastic sheets with thicknesses of about 0.4±0.2 mm as spacers, another silanized glass slide was placed on top and held firmly in place using binder clips. A light source (ILC Technology, Inc. Xenon Light Source with Fiber Optics) was adjusted to about a 5-cm distance from the glass slide using clamps and a stand. The center of the disc was illuminated; both sides of the disc were illuminated, for two minutes each.

The clips, the glass slide, and the spacers were carefully removed. With a spatula and tweezers, the discs were removed and weighed on a clean, tared silanized glass slide. The disc was placed into a heat-sealed membrane bag, as described in more detail below. One 20 µL disc was placed in each bag. The bag was heat-sealed, placed in 2.0 mL of phosphate buffer release media (0.01% $NaN_3$, 0.05M PBS, pH 7.4), placed on an orbital shaker turning at 100 rpm, and incubated at 39° C.

For each time point, the bag was placed into fresh 2.0 mL of PBS Release Media. Samples were collected for analysis every day for as long as the bST was being released.

Membrane bags were prepared as follows. Membrane sheets were cut into pieces of approximately 7×2.5 cm. The sheets were folded in half. Using a Bunsen burner or a propane torch, a spatula was heated until it became red. The edges of the sheets were aligned, and the side of the membrane was cut with the red-hot tweezer to seal the sides. Once the disc was placed into the bag, the last side was sealed using the same heat-sealing technique.

The samples were analyzed daily by SEC-HPLC. Monomers, dimers, and soluble aggregates could be detected using this method. The mobile phase used was 0.08M TFA in 60/40% $CH_3CN/H_2O$, adjusted to pH 2.0, isocratic, with a flow rate of 1.5 mL/min. The signals were detection at a wavelength of 220 nm. The column used was a Bio-Rad Bio-Sil® SEC 250, 5µ particle size, 300×7.8 mm ID, equipped with a guard column (Bio-Rad Bio-Sil® SEC 250 Guard, 5µ particle size, 80×7.8 mm ID). The injection volume was 10 µL. The standard calibration curves were 0, 0.1, 0.25, 0.5, 0.75, and 1 mg/mL bST in the mobile phase.

Figure 3:
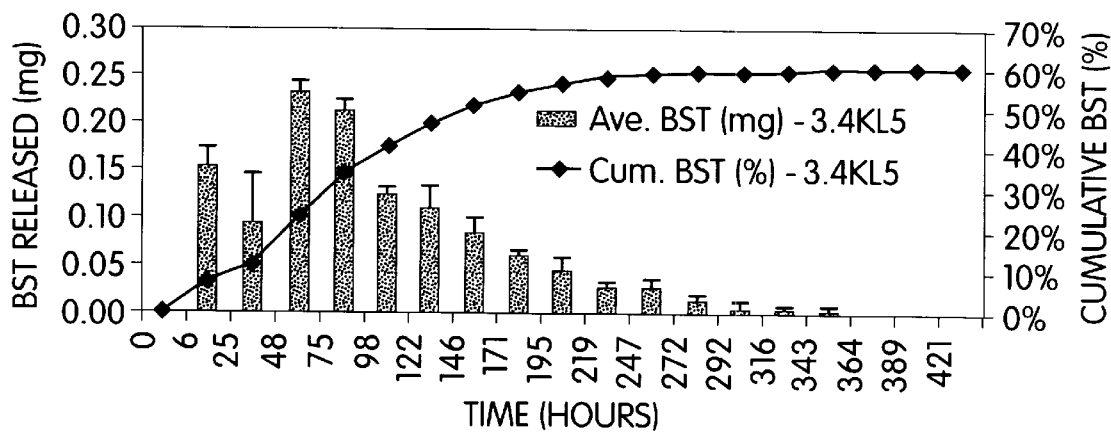
FIG. 3 is a graph showing the release profile of bST from a blend of 3.4KL4 and PEGDA.

The results are shown in FIG. 3. As shown there, bST was released over 14 days. No detectable levels of dimers or soluble aggregates were apparent in the release media. There was a minimal initial release of 12% on each of the first two days, followed by a moderate release rate.

EXAMPLE 6

Short Term Release of Insulin

Device Preparation: A degradable macromer (3.4KL5) was used. The protein used was Zn-Insulin (purchased from Sigma). The protein was loaded at a loading of 47%, based on dry weight. Three samples were prepared.

The samples were prepared as described in Example 4. The samples were analyzed by SEC-HPLC for the detection of monomers, dimers and soluble aggregates, using the conditions described in Example 5.

Figure 4:
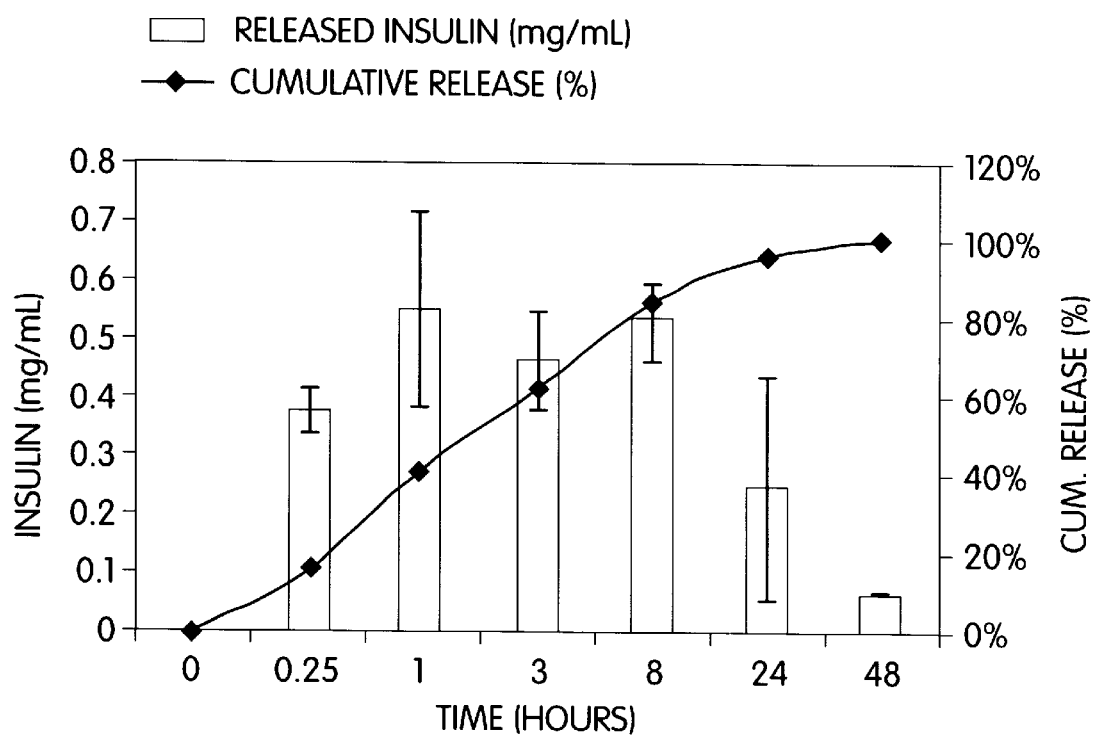
FIG. 4 is a graph showing the release profile of insulin from 3.4KL5.

The results are shown in FIG. 4. Insulin was released over 24 hours; no dimers or soluble aggregates were detected. Complete release (100%) was achieved within 24 hours.

EXAMPLE 7

Drug Release from Blends of Insoluble and Soluble Macromers

Devices were prepared as describe above. Macromers containing a blend of a soluble macromer (3.4KL5) and an insoluble macromer (3.4KC6) were used in a ratio of 50:50. The protein used was ZnbST (Protiva/Monsanto); it was loaded at a loading of 25%, based on dry weight. Six samples were prepared. The samples were analyzed by SEC-HPLC, as described above. The samples were monitored for the presence of monomers, dimers and soluble aggregates.

Figure 5:
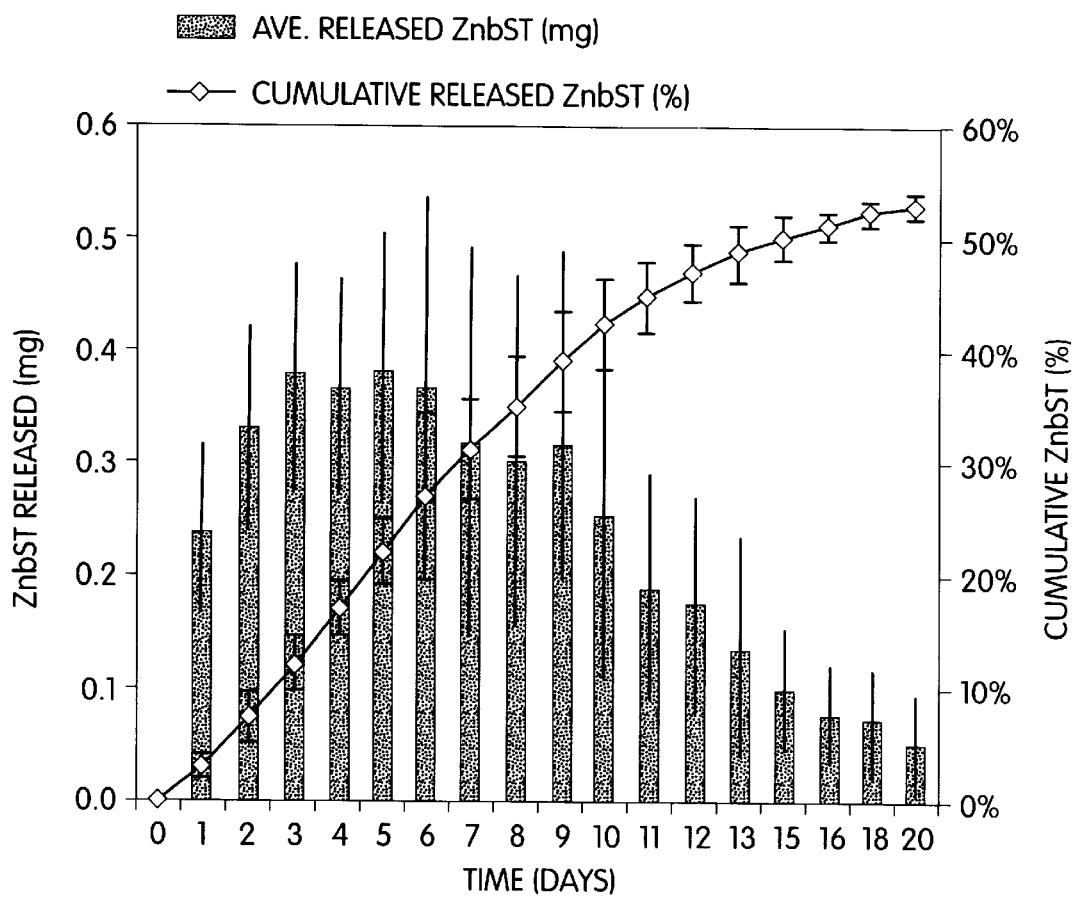
FIG. 5 is a graph showing the daily and cumulative release of ZnbST from a 50:50 blend of 3.4 5KC6 and 3.4 5KL6.

The results are shown in FIG. 5. A release of ZnbST over 20 days was observed; very low concentrations (less than 2%) of dimers or soluble aggregates were detected. In addition, no initial burst release was observed.

EXAMPLE 8

Drug Release from Blends of Insoluble and Soluble Macromers

Devices were prepared as describe above. A blend of a soluble macromer (3.4KL5) and an insoluble macromer (3.4KC6) were used, in a ratio of 75:25. The protein ZnbST (Protiva/Monsanto) was loaded at a loading of 25%, based on dry weight. Six samples were prepared. The samples were analyzed by SEC-HPLC to detect monomers, dimers, and soluble aggregates, as described above.

Figure 6:
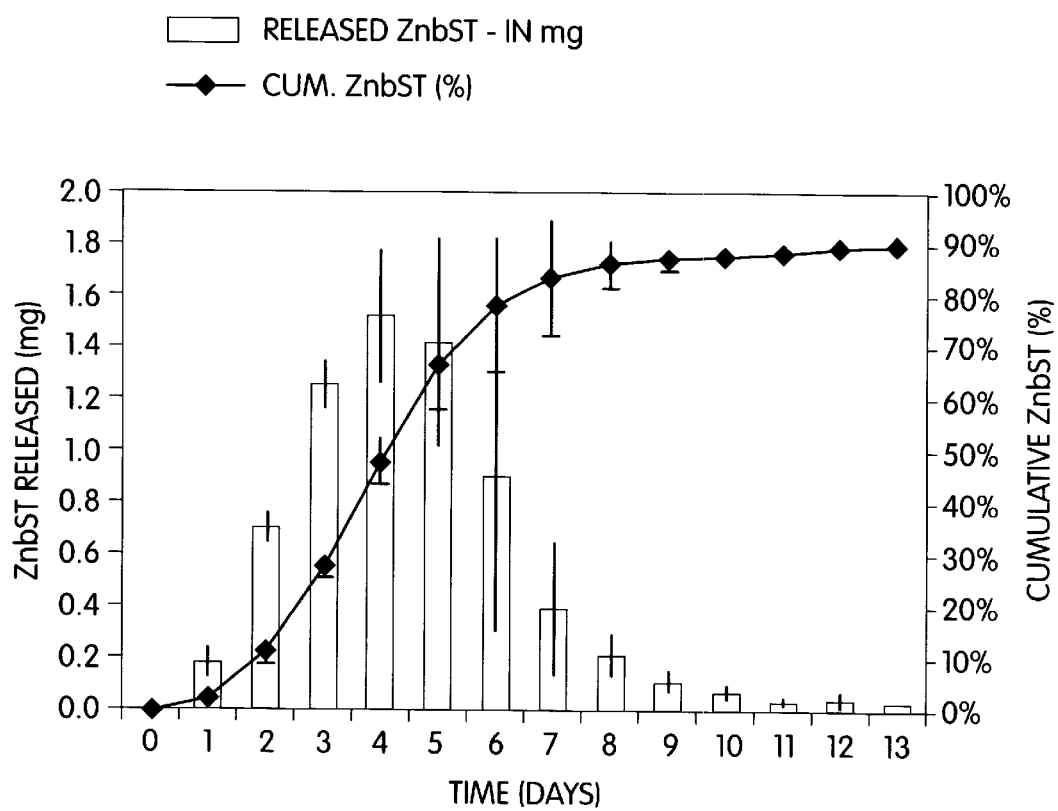
FIG. 6 is a graph showing the daily and cumulative release of ZnbST from a 75:25 blend of 3.4KL5 and 3.4KC6.
Figure 7:
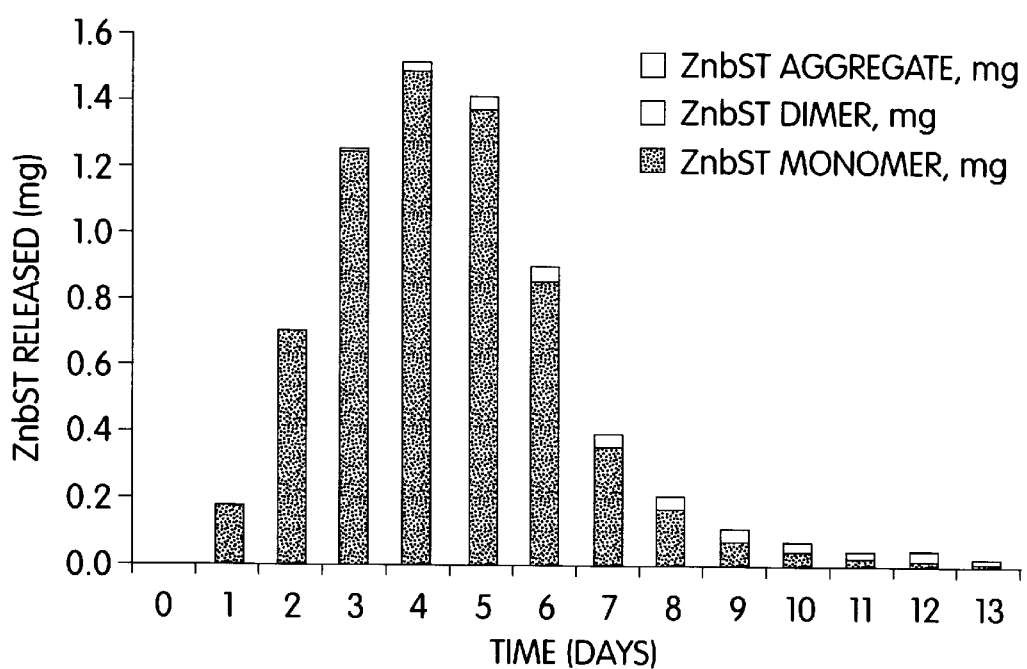
FIG. 7 is a graph showing the daily release of ZnbST monomer, dimer, and solubilizable monomer from a 75:25 blend of 3.4KL5 and 3.4KC6.

The results are shown in FIGS. 6 and 7. A long release of ZnbST over 17 days was observed; within 13 days of release, 90% of the incorporated ZnbST was released. Very little dimer or aggregate was released.

EXAMPLE 9

Controlled Release of Bovine Somatotropin in Hypophysectomized Rats

The controlled delivery of active bovine somatotropin (MW 20 Kd) was confirmed in the hypophysectomized rat model. Hypophysectomized female rats were purchased from Taconic Labs (Germantown, N.Y.). The rats were weighed each morning. Prior to the initiation of the study, the rats were held 7 days to confirm lack of growth. On day 1 of the study the rats weighed 118±1.5 grams (mean±sem, n=18). The rats were divided into 3 groups of equal mean weights. Group 1 remained untreated and served as a negative control. Group 2 received an implant of bST in a hydrogel made of a blend of 3:1 of 3.4KL5 and PEGDA (each device contained 0.9 to 1.1 mg of bST). The rats in Group 3 were injected with 100 µg bST subcutaneously each day for the duration of the study.

Figure 8:
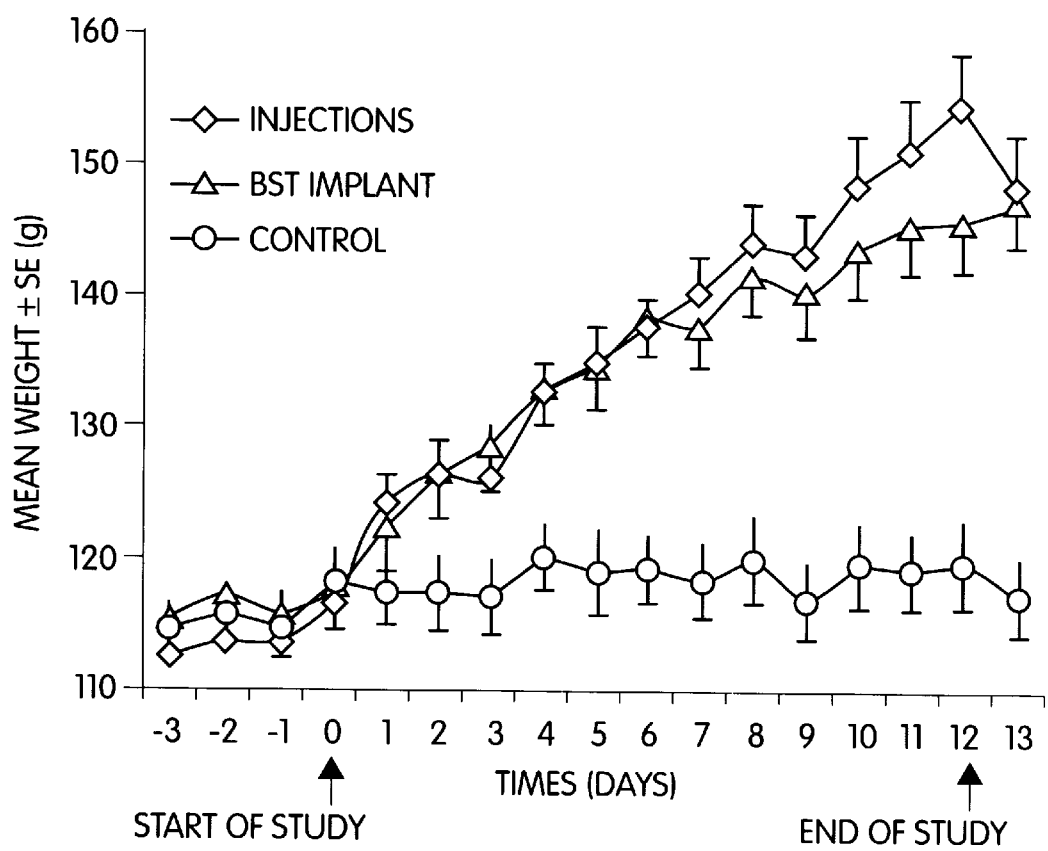
FIG. 8 is a graph showing the effect of bST injections and a sustained delivery bST formulation on the growth of hyphysectomized rats.

The results are shown in FIG. 8. The untreated control group did not grow during the study, and after 11 days weighed an average of 119±2.9 grams. The rats of Group 3, which received 100 µg bST daily during the study, exhibited continued growth and weighed 151±4 grams after 11 days of treatment. The rats of Group 2 grew at a rate similar to the rats of Group 3, and weighed 145±3.7 g after 11 days (p=032 for the comparison with Group 3, t-test).

EXAMPLE 10

Release of bST

A macromer mixture containing approximately 30% (w/w) of bST was prepared using the methods described above. The macromer/protein mixture was put in a glass cylinder having an internal diameter of either 1.12 mm or 0.61 mm. The system was exposed to light for 20 seconds, removed from the glass cylinder, placed on aluminum foil, and exposed to light for an additional 3.5 minutes. The resulting hydrogel cylinders were placed in 1 mL of release media (PBS, pH 7.4), and the released bST was monitored by HPLC. Initial data indicated that the release from the larger diameter cylinder closely trailed the release from the small diameter cylinder. In addition, the characteristics of the bST release indicated degradation/swelling of a controlled system. The system showed the following fraction release $M/M_\infty$ as a power function of time t for a short time-period: $M/M_\infty = k't^n$, where k' is a constant characteristic of the system and n is an exponent characteristic of the mode of transport. For n=0.5, the drug release follows a Fickian-diffusion mechanism. For n>0.5, non-Fickian behavior was observed.

Figure 9:
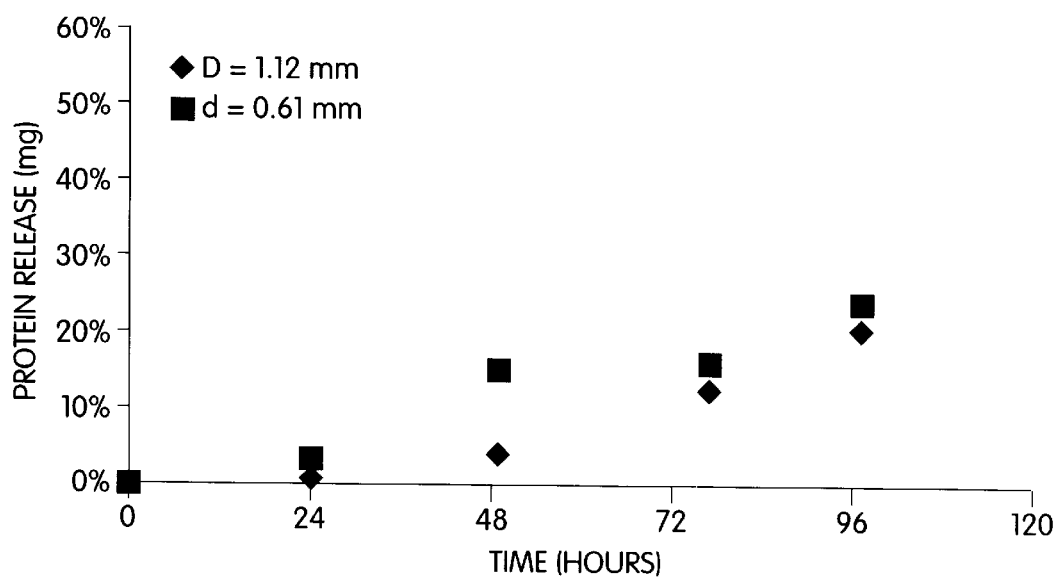
FIG. 9 is a graph showing the initial release of bST from cylindrical hydrogel devices with small and large diameters.

When the data presented in FIG. 9 was analyzed for erosion/diffusion release mechanisms. The large cylinder had a value of $M/M_\infty = 1E-06t^2$, and the smaller cylinder had a value of $M/M_\infty = 3E-05t^2$. Therefore when n=2, non-Fickian behavior was observed.

In a different analysis based only on diffusion, the flux from the cylinder was analyzed using the following Fickian equation:

$$J = D^* A^* \Delta C/\Delta X,$$

where J is the flux; D is the diffusion constant; A is the surface area; C is the concentration in the cylinder; and S is the distance from the center. In this analysis the flux should differ dramatically whether the release occurred from either a large or a small diameter cylinder. Theoretical analysis predicted that under Fickian diffusion, when the smaller diameter cylinder released 20%, the larger diameter cylinder would release 7% of the incorporated drug. It was observed, however, that when the smaller diameter cylinder released 20%, the larger diameter cylinder released 16%. Therefore, non-Fickian behavior was observed.

In these hydrogel systems, the initial release phase involved water uptake (swelling); as a result, the homogeneous drug concentration profile within the matrix became sigmoidal. A high drug concentration exists in the center of the cylinder, and very little or no drug is available at the circumference of the device. Such cylindrical systems yield release kinetics independent of the radius of the cylinder. A detailed description of this phenomenon can be found in Ping I. Lee, "Diffusion Controlled Matrix Systems," in *Treatise on Controlled Drug Delivery*, Kydonicus, A., ed. pp. 155–197 (1992).

EXAMPLE 11

Controlled Release of Erythropoeitin in Rats

The controlled delivery of active human erythropoeitin (EPO) was confirmed in male Sprague-Dawley rats purchased from Taconic Labs (Germantown, N.Y.). Hydrogel devices were manufactured to contain 3000 Units per device, as described in Example 14. These devices were prepared in the absence of vinyl pyrrolidone, and other polymerizable monovinyl monomers. One of these devices was implanted in each of 3 rats. Three other rats received a subcutaneous injection of EPO (1000 Units) daily for 3 days. A control group of 3 rats received no treatment.

On day 5 after implantation of the device or the start of the subcutaneous injections, venous blood samples were obtained from each rat and stored in EDTA. The fraction of reticulocytes (immature red blood cells) was determined after staining with Acridine Orange by automated flow cytometry.

Figure 10:
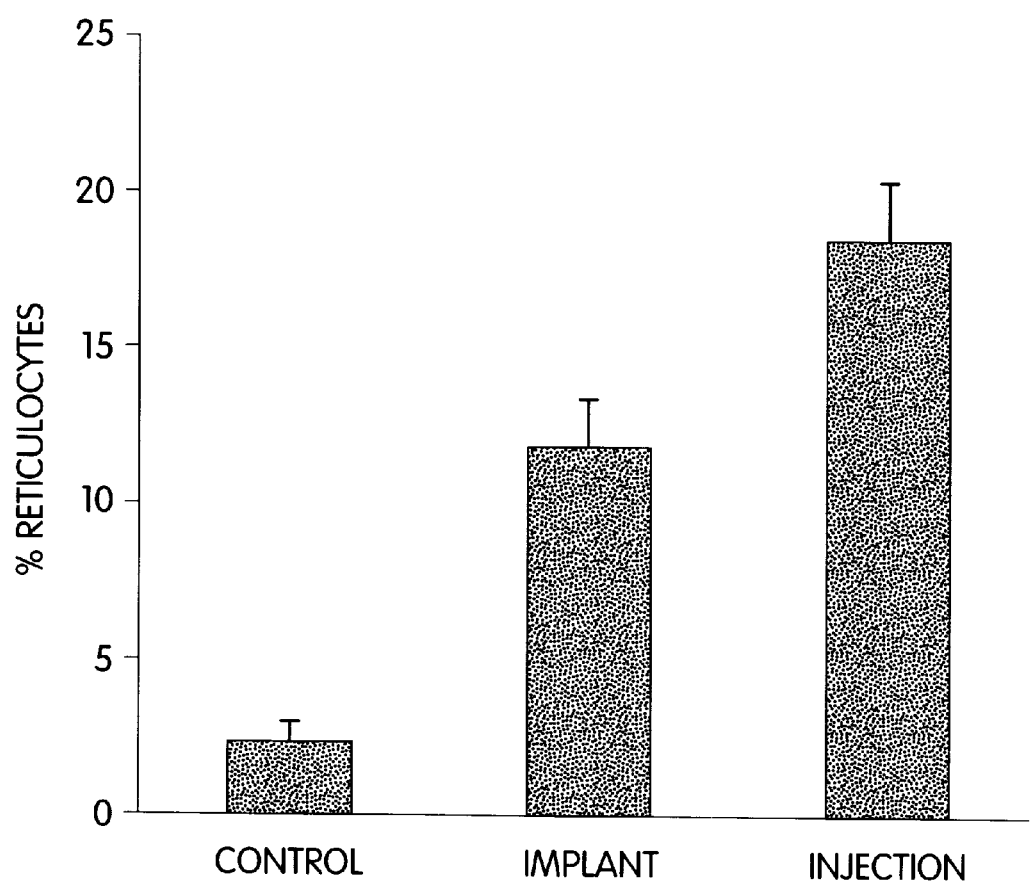
FIG. 10 is a graph showing the effect of EPO injections and a sustained delivery EPO formulation on the percentage of reticulocytes.

The results are shown in FIG. 10. As shown there, the rats in the control group had about 2.5% reticulocytes. The rats with the implants had about 12% reticulocytes, and the rats that received injections had about 19% reticulocytes after five days.

EXAMPLE 12

Controlled Release of Insulin in Diabetic Rats

Sprague-Dawley rats were purchased from Taconic Labs (Germantown, N.Y.). Diabetes was induced by treatment with streptozotocin (65 mg/kg, i.v.) and confirmed 48 hours later by elevation of blood glucose (>300 mg/dL). Following anesthesia of the rat with pentobarbital (35 mg/kg), a catheter was placed in a jugular vein. After a baseline blood sample was taken for the determination of blood glucose concentration, a hydrogel device containing 1 Unit of insulin was implanted subcutaneously. The devices were prepared in the absence of vinyl pyrrolidone, and other polymerizable monovinyl monomers. Blood samples were taken at 15, 30, 60, 120, and 180 minutes after implantation of the device and were used to determine blood glucose levels.

Figure 11:
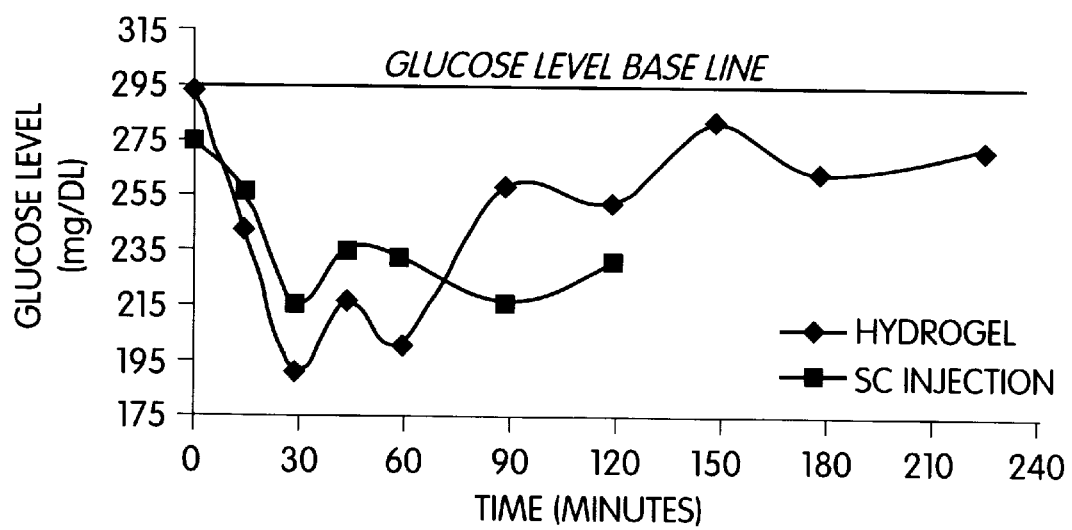
FIG. 11 is a graph showing the effect of subcutaneous insulin injections and a subcutaneous sustained release hydrogel insulin formulation on blood glucose levels of diabetic rats.

The results are shown in FIG. 11. As shown there, the blood glucose level dropped. This demonstrates that the devices are capable of releasing insulin in its active form.

To test the pulmonary delivery system, the neck was opened with a midline incision and the trachea exposed by blunt dissection. A slit was cut into the trachea, and a small polyethylene tube was advanced distally into the lung. A small volume of insulin-containing hydrogel microparticles (total dose was 3 Units insulin) was instilled into the lung and the tube removed. Blood samples were taken and analyzed as described above for the subcutaneous device.

Figure 12:
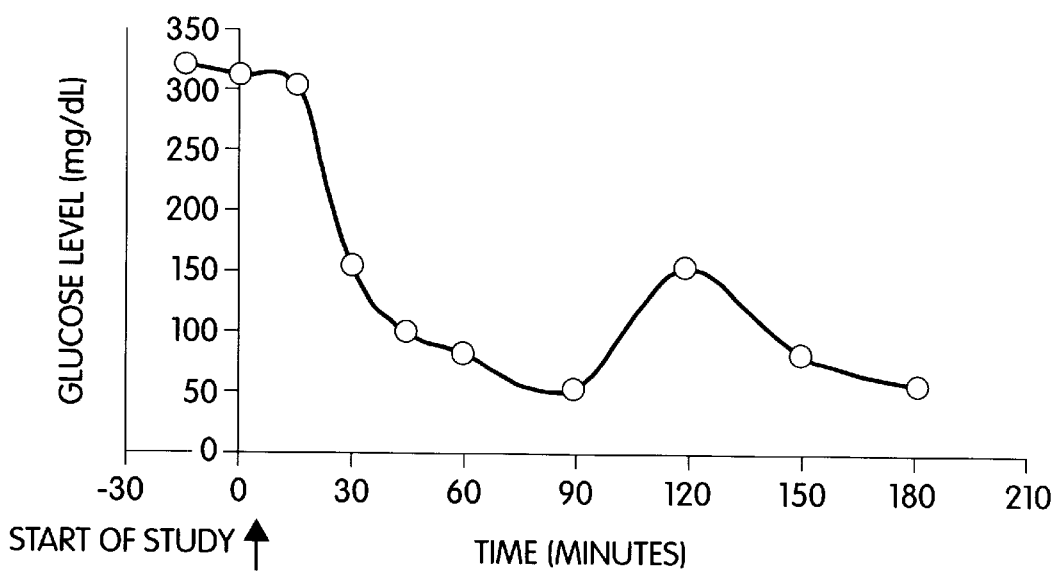
FIG. 12 is a graph showing the effect of pulmonary sustained release hydrogel formulation insulin on blood glucose levels of diabetic rats.

The results are shown in FIG. 12. Glucose levels dropped significantly within 30 minutes and remained low (below 150 mg/dl) for at least 180 minutes.

EXAMPLE 13

Controlled Release of Human Growth Hormone in Hypophysectomized Rats

The controlled delivery of active human growth hormone (hGH, MW 20 Kd) was confirmed in the hypophysectomized rat model. Hypophysectomized female rats purchased from Taconic Labs (Germantown, N.Y.) were weighed each morning. Prior to the initiation of the study the rats were held 7 days to confirm lack of growth. The rats were divided into 3 groups of equal mean weights. Group 1 remained untreated and served as a negative control. Group 2 received an implant of hGH in a hydrogel made of a 3:1 blend of 3.4KL5 and 3.4KC6 (each device contained approximately 1 mg of hGH). The rats in Group 3 were injected with 100 μg hGH subcutaneously each day for the duration of the study.

Initial results indicate that the previous results obtained with bST were reproducible using hGH. The untreated control group did not grow during the study. The rats of Group 3, which received 100 μg hGH daily during the study, exhibited continued growth. The rats of Group 2 grew at a rate similar to the rats of Group 3.

EXAMPLE 14

Release of EPO from Macromers

To a sterile 20 mL vial were added: 0.0330 g of TEOA (neat), 1.0076 g of 3.4KL5, 0.0598 g of 1000 ppm cosin (in PBS, pH 7.0), and 2.32 g solution of EPO (10,000 units/mL). No vinyl pyrrolidone, or other polymerizable monovinyl monomer was added. The resulting mixture was mixed and polymerized by light (ILC Technology, Inc. Xenon Light Source with Fiber Optics).

The rate of in vitro release was conducted by averaging the release from 3 discs containing an average of 2500 units per disc. The release was conducted in 4 mL of PBS (pH 7.4) at 39° C. The release media was exchanged daily. Analysis was done by size exclusion chromatography. (HPLC: model 2690 by waters, Column: SEC 250 by BioRad, mobile phase: 0.8M TFA in 60% acetonitrile @1.5 mL/min, detector wavelength: 220 nm).

Figure 13:
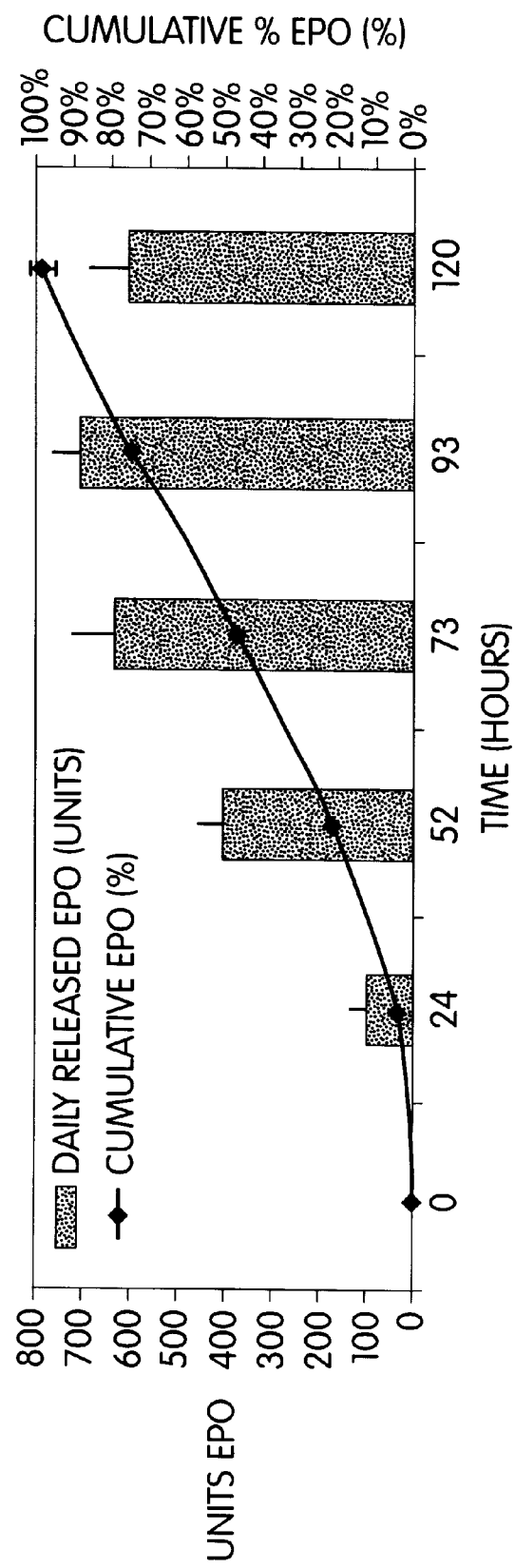
FIG. 13 is a graph showing the in vitro release rate of EPO from 3.4KL5.

The results are shown in FIG. 13. As shown there, EPO was released for at least 120 hours. After 120 hours, over 500 units of EPO were still being released.

EXAMPLE 15

Release of Insulin from Macromer Particles

To a sterile 20 mL vial were added: 0.2559 g of 200 mM of TEOA (in PBS buffer, pH 7.0), 0.2548 g of 3.4KL5, 0.0206 g of 1000 PPM eosin (in PBS, pH 7.0) and 0.0615 g of insulin (Sigma). No vinyl pyrrolidone, or other polymerizable monovinyl monomer was added. The resulting mixture was mixed and placed into 10 mL glass tubes. The tubes were exposed to xenon light (ILC Technology, Inc. Xenon Light Source with Fiber Optics) for 10 seconds. The semi-cured hydrogel was pushed out of the glass tube and further polymerized for 3.5 minutes. The cured hydrogel rods were placed in 15 mL of heptane and ground using a homogenizer (Silverson L4RT-A) for 30 seconds @5000 rpm, followed by 30 seconds @3000 rpm. The heptane was decanted, and the powder was dried under nitrogen. The resulting particles had a size distribution from 2 mm to 500 mm.

Particles (16 mg) were placed in a porous (0.8 mm) "release-bag" (described in Example 5). The in vitro release was calculated by averaging the release from 2 release bags. The release-bag was placed into 2 mL of PBS (pH 7.4) at 39° C. The release media was exchanged every 15 minutes for the first 2 hours and every 30 minutes thereafter. Analysis was done by size exclusion chromatography. (HPLC: model 2690 by waters, Column: SEC 250 by BioRad, mobile phase: 0.8M TFA in 60% acetonitrile @1.5 mL/min, detector wavelength: 220 nm).

Figure 14:
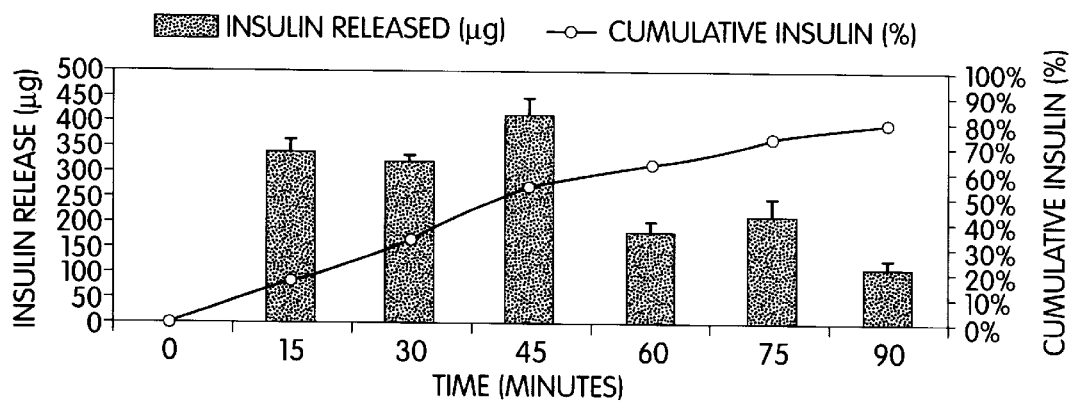
FIG. 14 is a graph showing in vitro release of insulin from 3.4KL5 particles.

The results are shown in FIG. 14. As shown there, insulin was released over 90 minutes. After 90 minutes, 100 μg of insulin was still being released.

EXAMPLE 16

Release of Luteinizing Hormone Releasing Hormone (LHRH)

To a 20 mL vial are added: 0.2559 g of 200 mM of TEOA (in PBS buffer, pH 7.0), 0.2548 g of IKC3, 0.0206 g of 1000 PPM eosin (in PBS, pH 7.0) and 0.0615 g of LHRH (Sigma). No vinyl pyrrolidone, or other polymerizable monovinyl monomer is added. The resulting mixture is placed between two glass sheets and polymerized by xenon light (ILC Technology, Inc. Xenon Light Source with Fiber Optics) for 2 minutes on each side. The final hydrogel sheet is cryo-milled to produce an injectable powder.

EXAMPLE 17

Pulmonary Devices Containing Human Growth Hormone (hGH)

To a 20 mL vial are added: 0.2559 g of 200 mM of TEOA (in PBS buffer, pH 7.0), 0.2548 g of 3.4KL5, 0.0206 g of 1000 PPM eosin (in PBS, pH 7.0) and 0.0615 g hGH (Genentech's hGH injectable formulation, purified by a Millipore Centricon™). No vinyl pyrrolidone, or other polymerizable monovinyl monomer is added. The resulting mixture is stirred and placed into 10 mL glass tubes. The tubes are exposed to xenon light (ILC Technology, Inc. Xenon Light Source with Fiber Optics) for 10 seconds. The semi-cured hydrogel is pushed out of the glass tube and further polymerized for 3.5 minutes. The cured hydrogel rods are put into 15 mL of heptane and are ground using a homogenizer (Silverson L4RT-A) for 30 seconds @5000 rpm, followed by 30 seconds @3000 rpm. The heptane is decanted, and the powder is dried under nitrogen. The powder is used for pulmonary, oral, or subcutaneous sustained delivery of hGH.

EXAMPLE 18

Release of GLP-1

GLP-1 (glucacon like peptide-1) is a peptide drug that has shown promise in the treatment of Type II diabetics. To a 20 mL vial are added: 0.2559 g of 200 mM of TEOA (in PBS buffer, pH 7.0), 0.2548 g of 1 KC3, 0.0206 g of 1000 PPM cosin (in PBS, pH 7.0) and 0.0615 g of GLP-1. The resulting mixture is placed between two glass sheets and polymerized by xenon light (ILC Technology, Inc. Xenon Light Source with Fiber Optics) for 2 minutes on each side. The final hydrogel sheet is cryo-milled to produce an injectable powder.

EXAMPLE 19

Oral Formulation for Release of Proteins

Using the procedure of Example 15, one of insulin, human growth hormone, human alpha interferon, or erythropoietin is incorporated into macromer particles. Using cryomilling or the milling procedure of Example 15, very small microparticles are produced, preferably of an average size of less than about 500 nanometers. Such nanoparticles are then introduced into the rat GI tract surgically, using catheter infusion into the upper GI tract. The dosing of such nanoparticles is based upon the assumption that about 0.5% of the drug in the nanoparticles will be detectable in the blood of such rats, e.g., by RIA, with the specific pharmacology of each drug taken into account.

In the case of insulin, blood samples are taken at time t=−15, 0, 30, 60, 90, 120, and 180 minutes, and monitored for insulin by RIA and for blood glucose by glucometer (when insulin is being administered, diabetic rats are utilized).

For other drugs, normal rats are used and blood drug levels are measured at these same time points using RIA or ELIZA techniques.

In addition to the above procedures, the above drug-containing microspheres can be modified to enhance their absorption in the small intestine, colon, and other appropriate areas of the GI tract. Such modifications can include precipitating lipid bilayers around the microcapsules so they appear as fat-like particles from digested food, linking molecules such as ferritin to the particles, or putting a charged layer on the outside of the microparticles.

OTHER EMBODIMENTS

From the foregoing description, it will be apparent that variations and modifications may be made to the invention described herein to adopt it to various usages and conditions. Such embodiments are also within the scope of the following claims.

All publications and patents mentioned in this specification are herein incorporated by reference to the same extent as if each individual publication or patent was specifically and individually indicated to be incorporated by reference.

What is claimed is:

1. A method for making a controled release therapeutic composition for delivery of a biologically active substance, said method comprising the steps of:
    (a) combining said biologically active substance with a macromer;
    (b) forming a mixture of the combination formed in step (a); and
    (c) polymerizing said mixture to form articles;
wherein said article comprises at least 5% active substance by weight.

2. The method of claim 1, wherein the time during which 10% of the releasable active substance is released is greater than $\frac{1}{10}$ of the $t_{50}$.

3. A method for delivering a biologically active substance, said method comprising
    administering the articles of claim 1 to a mammal.

4. The method of claim 3, wherein step (d) comprises administering said articles to the lung of said mammal.

5. The method of claim 3, wherein step (d) comprises administering said articles intravenously.

6. The method of claim 3, wherein step (d) comprises administering said articles subcutaneously.

7. The method of claim 3, wherein step (d) comprises administering said articles intramuscularly.

8. The method of claim 3, wherein step (d) comprises administering said articles orally.

9. The method of claim 3, wherein step (d) comprises administering said articles nasally.

10. The method of claim 3, wherein said mammal is a human.

11. The method of claim 3, wherein said biologically active substance is a protein.

12. The method of claim 1, wherein said biologically active substance is a protein.

13. The method of claim 1, wherein said macromer is soluble.

14. The method of claim 1, wherein said macromer is insoluble.

* * * * *